(12) United States Patent
Liverton et al.

(10) Patent No.: US 9,695,163 B2
(45) Date of Patent: Jul. 4, 2017

(54) THIAZOLE OREXIN RECEPTOR ANTAGONISTS

(71) Applicant: MERCK SHARP & DOHME CORP., Rahway, NJ (US)

(72) Inventors: Nigel Liverton, Harleysville, PA (US); Douglas C. Beshore, West Point, PA (US); Scott D. Kuduk, Doylestown, PA (US); Yunfu Luo, Shanghai (CN); Na Meng, Shanghai (CN); Tingting Yu, Shanghai (CN)

(73) Assignee: MERCK SHARP & DOHME CORP, Rahway, NJ (US)

(*) Notice: Subject to any disclaimer, the term of this patent is extended or adjusted under 35 U.S.C. 154(b) by 0 days.

(21) Appl. No.: 14/910,548

(22) PCT Filed: Aug. 4, 2014

(86) PCT No.: PCT/US2014/049541
§ 371 (c)(1),
(2) Date: Feb. 5, 2016

(87) PCT Pub. No.: WO2015/020933
PCT Pub. Date: Feb. 12, 2015

(65) Prior Publication Data
US 2016/0185768 A1    Jun. 30, 2016

(30) Foreign Application Priority Data
Aug. 8, 2013  (WO) ............... PCT/CN2013/081078

(51) Int. Cl.
C07D 417/14   (2006.01)
C07D 417/04   (2006.01)

(52) U.S. Cl.
CPC ......... *C07D 417/14* (2013.01); *C07D 417/04* (2013.01)

(58) Field of Classification Search
CPC .......................... C07D 417/14; C07D 417/04
See application file for complete search history.

(56) References Cited

U.S. PATENT DOCUMENTS

| | | | |
|---|---|---|---|
| 8,163,775 B2 | 4/2012 | Bessis et al. | |
| 8,242,121 B2 | 8/2012 | Coleman et al. | |
| 8,357,700 B2 | 1/2013 | Cox et al. | |
| 8,357,709 B2 | 1/2013 | Coleman et al. | |
| 8,466,281 B2 | 6/2013 | Coleman et al. | |
| 8,669,272 B2 | 3/2014 | Breslin et al. | |
| 8,710,076 B2 | 4/2014 | Breslin et al. | |
| 8,940,898 B2 | 1/2015 | Kuduk et al. | |
| 9,029,364 B2 | 5/2015 | Kuduk et al. | |
| 2004/0215014 A1* | 10/2004 | Chan ................. | C07D 401/14 540/596 |
| 2007/0173494 A1 | 7/2007 | Powers et al. | |
| 2011/0201632 A1 | 8/2011 | Breslin et al. | |
| 2011/0201652 A1 | 8/2011 | Cox et al. | |
| 2011/0251237 A1 | 10/2011 | Breslin et al. | |
| 2014/0228377 A1* | 8/2014 | Abe ..................... | C07D 498/04 514/256 |
| 2015/0252033 A1 | 9/2015 | Kuduk et al. | |
| 2015/0291558 A1 | 10/2015 | Kuduk et al. | |
| 2015/0322039 A1 | 11/2015 | Kuduk et al. | |
| 2015/0322040 A1 | 11/2015 | Kuduk et al. | |
| 2015/0322041 A1 | 11/2015 | Kuduk et al. | |
| 2015/0322074 A1 | 11/2015 | Cooke et al. | |
| 2016/0016935 A1 | 1/2016 | Kuduk et al. | |
| 2016/0068510 A1 | 3/2016 | Kuduk et al. | |
| 2016/0068514 A1 | 3/2016 | Kuduk | |

FOREIGN PATENT DOCUMENTS

| | | |
|---|---|---|
| WO | WO2005003128 | 1/2005 |
| WO | WO2005074934 | 8/2005 |
| WO | WO2010124055 | 10/2010 |
| WO | WO2013005755 | 1/2013 |
| WO | WO2013059222 | 4/2013 |
| WO | WO2014099696 | 6/2014 |
| WO | WO2014137883 | 9/2014 |
| WO | WO2014176142 | 10/2014 |
| WO | WO2014176144 | 10/2014 |
| WO | WO2014176146 | 10/2014 |
| WO | WO2015088864 | 6/2015 |
| WO | WO2015088865 | 6/2015 |
| WO | WO2015095108 | 6/2015 |
| WO | WO2015095442 | 6/2015 |

* cited by examiner

*Primary Examiner* — Timothy Thomas
(74) *Attorney, Agent, or Firm* — J. Eric Thies; John C. Todaro

(57) ABSTRACT

The present invention is directed to thiazole compounds which are antagonists of orexin receptors. The present invention is also directed to uses of the thiazole compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the prevention or treatment of such diseases in which orexin receptors are involved.

14 Claims, No Drawings

THIAZOLE OREXIN RECEPTOR ANTAGONISTS

CROSS REFERENCE TO RELATED APPLICATIONS

This application is a U.S. National Phase application under 35 U.S.C. §371 of PCT Application No. PCT/US2014/049541, filed Aug. 4, 2014, which claims priority from PCT/CN2013/081078, filed Aug. 8, 2013.

BACKGROUND OF THE INVENTION

The orexins (hypocretins) comprise two neuropeptides produced in the hypothalamus: orexin A (OX-A) (a 33 amino acid peptide) and orexin B (OX-B) (a 28 amino acid peptide) (Sakurai T. et al., *Cell,* 1998, 92:573-585). Orexins are found to stimulate food consumption in rats suggesting a physiological role for these peptides as mediators in the central feedback mechanism that regulates feeding behavior (Sakurai T. et al., 1998, supra). Orexins regulate states of sleep and wakefulness opening potentially novel therapeutic approaches for narcoleptic or insomniac patients (Chemelli R. M. et al., *Cell,* 1999, 98:437-451). Orexins have also been indicated as playing a role in arousal, reward, learning and memory (Harris, et al., *Trends Neurosci.,* 2006, 29:571-577). Two orexin receptors have been cloned and characterized in mammals. They belong to the super family of G-protein coupled receptors (Sakurai T. et al., *Cell,* 1998, supra): the orexin-1 receptor (OX1 or OX1R) is selective for OX-A, and the orexin-2 receptor (OX2 or OX2R) is capable of binding OX-A as well as OX-B. The physiological actions in which orexins are presumed to participate are thought to be expressed via one or both of the OX1 receptor and the OX2 receptor as the two subtypes of orexin receptors.

SUMMARY OF THE INVENTION

The present invention is directed to thiazole compounds that are antagonists of orexin receptors. The present invention is also directed to uses of the thiazole compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the potential prevention or treatment of such diseases in which orexin receptors are involved.

DETAILED DESCRIPTION OF THE INVENTION

The present invention is directed to compounds of the formula I:

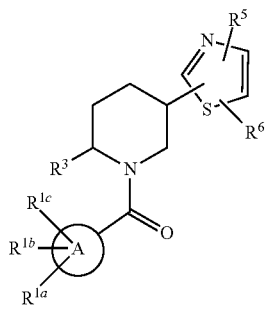

wherein:
A is selected from the group consisting of phenyl, naphthyl and heteroaryl;
$R^{1a}$, $R^{1b}$ and $R^{1c}$ are independently selected from the group consisting of:
(1) hydrogen,
(2) halogen,
(3) hydroxyl,
(4) —(C=O)$_m$—O$_n$—C$_{1-6}$alkyl, where the alkyl is unsubstituted or substituted with one or more substituents selected from $R^4$,
(5) —(C=O)$_m$—O$_n$—C$_{3-6}$cycloalkyl, where the cycloalkyl is unsubstituted or substituted with one or more substituents selected from $R^4$,
(6) —(C=O)$_m$—C$_{2-4}$alkenyl, where the alkenyl is unsubstituted or substituted with one or more substituents selected from $R^4$,
(7) —(C=O)$_m$—C$_{2-4}$alkynyl, where the alkynyl is unsubstituted or substituted with one or more substituents selected from $R^4$,
(8) —(C=O)$_m$—O$_n$-phenyl or —(C=O)$_m$—O$_n$-naphthyl, where the phenyl or naphthyl is unsubstituted or substituted with one or more substituents selected from $R^4$,
(9) —(C=O)$_m$—O$_n$-heterocycle, where the heterocycle is unsubstituted or substituted with one or more substituents selected from $R^4$,
(10) —(C=O)$_m$—NR$^9$R$^{10}$;
(11) —S(O)$_2$—NR$^9$R$^{10}$,
(12) —(CH$_2$)$_r$—S(O)$_q$—R$^9$, where r is 0, 1 or 2 (wherein if r is 0, a bond is present), q is 0, 1 or 2 and
(13) —CO$_2$H,
(14) —CN, and
(15) —NO$_2$;
$R^3$ is selected from C$_{1-6}$alkyl and C$_{3-6}$cycloalkyl, which is unsubstituted or substituted with one or more substituents selected from $R^4$;
$R^4$ is selected from the group consisting of:
(1) hydroxyl,
(2) halogen,
(3) C$_{1-6}$ alkyl,
(4) —C$_{3-6}$cycloalkyl,
(5) —O—C$_{1-6}$alkyl,
(6) —O(C=O)—C$_{1-6}$alkyl,
(7) —NH$_2$,
(8) —NH—C$_{1-6}$alkyl,
(9) —NO$_2$,
(10) phenyl,
(11) heterocycle,
(12) —CO$_2$H, and
(13) —CN;
$R^5$ and $R^6$ are independently selected from the group consisting of:
(1) hydrogen,
(2) halogen,
(3) C$_{1-6}$alkyl, which is unsubstituted or substituted with halogen, hydroxyl, —O—C$_{1-6}$alkyl, —NR$^7$R$^8$, —(C=O)O—C$_{1-6}$alkyl or phenyl,
(4) C$_{3-6}$cycloalkyl, which is unsubstituted or substituted with C$_{1-6}$alkyl, halogen or hydroxyl,
(6) —(C=O)O—C$_{1-6}$alkyl, which is unsubstituted or substituted with halogen, hydroxyl or phenyl
(7) —CN, and
(8) —(C=O)NR$^7$R$^8$;
$R^7$ and $R^8$ are independently hydrogen or C$_{1-6}$alkyl;
$R^9$ and $R^{10}$ are independently selected from the group consisting of:
(1) hydrogen,
(2) C$_{1-6}$alkyl, which is unsubstituted or substituted with $R^4$, (3) C$_{3-6}$alkenyl, which is unsubstituted or substituted with R$^4$,
(4) C$_{3-6}$alkynyl, which is unsubstituted or substituted with R$^4$,
(5) C$_{3-6}$cycloalkyl which is unsubstituted or substituted with R$^4$,
(6) phenyl, which is unsubstituted or substituted with R$^4$, and
(7) heterocycle, which is unsubstituted or substituted with R$^4$, m and n are independently 0 or 1 (wherein if m is 0 or n is 0, a bond is present);
r is 0, 1 or 2 (wherein if r is 0, a bond is present);
q is 0, 1 or 2;
or a pharmaceutically acceptable salt thereof.

An embodiment of the present invention includes compounds of the formula Ia:

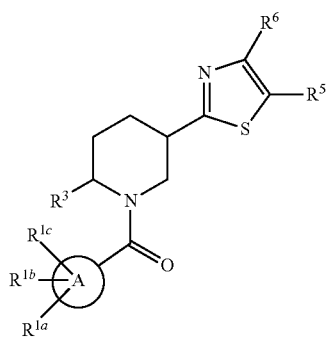

Ia wherein A, R$^{1a}$, R$^{1b}$, R$^{1c}$, R$^3$, R$^5$, and R$^6$ are defined herein; or a pharmaceutically acceptable salt thereof.

Embodiments of the present invention include compounds of the formula Ia' and formula Ia":

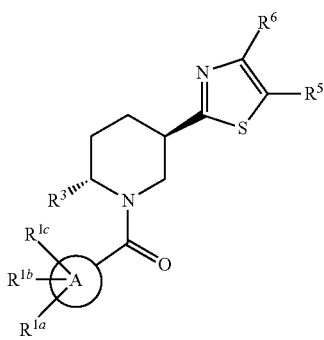

Ia'

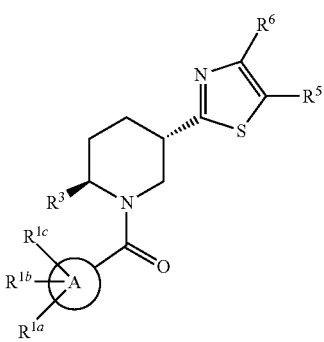

Ia"

wherein A, R$^{1a}$, R$^{1b}$, R$^{1c}$, R$^3$, R$^5$, and R$^6$ are defined herein; or a pharmaceutically acceptable salt thereof.

An embodiment of the present invention includes compounds of the formula Ib:

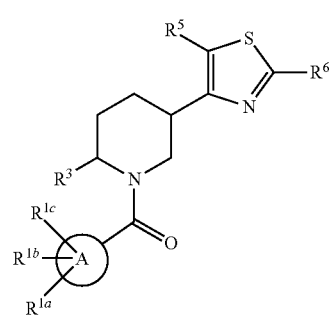

Ib wherein A, R$^{1a}$, R$^{1b}$, R$^{1c}$, R$^3$, R$^5$, and R$^6$ are defined herein; or a pharmaceutically acceptable salt thereof.

Embodiments of the present invention include compounds of the formula Ib' and formula Ib":

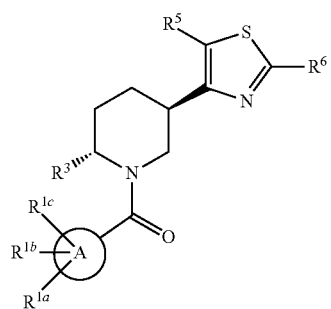

Ib'

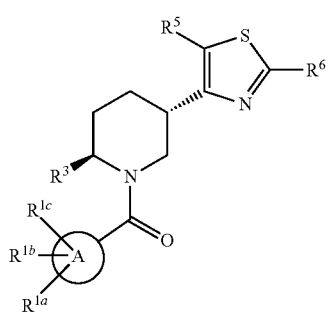

Ib"

wherein A, R$^{1a}$, R$^{1b}$, R$^{1c}$, R$^3$, R$^5$, and R$^6$ are defined herein; or a pharmaceutically acceptable salt thereof. In a further embodiment, R$^5$ is hydrogen.

An embodiment of the present invention includes compounds of the formula Ic:

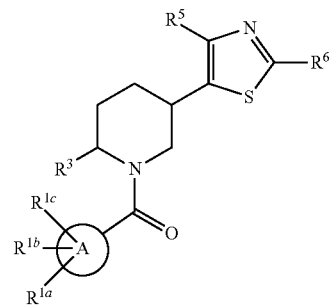

Ic wherein A, R$^{1a}$, R$^{1b}$, R$^{1c}$, R$^3$, R$^5$, and R$^6$ are defined herein; or a pharmaceutically acceptable salt thereof.

Embodiments of the present invention include compounds of the formula Ic' and formula Ic":

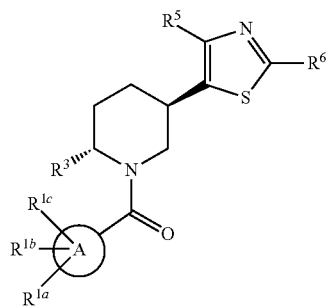

Ic'

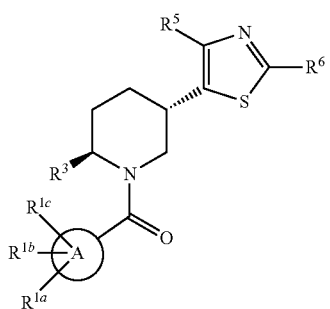

Ic"

wherein A, $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Id:

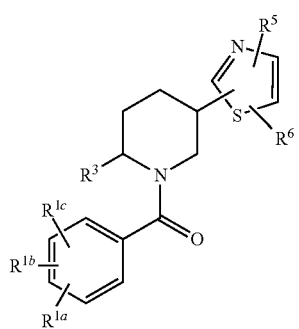

Id wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Ie:

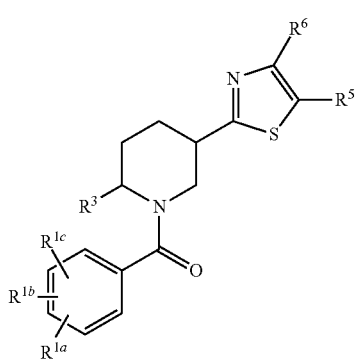

Ie wherein $R^{1a}$, $R^{1b}$, $R^{1c}$, $R^3$, $R^5$, and $R^6$ are defined herein; or a pharmaceutically acceptable salt thereof.

Embodiments of the present invention include compounds of the formula Ie' and formula Ie":

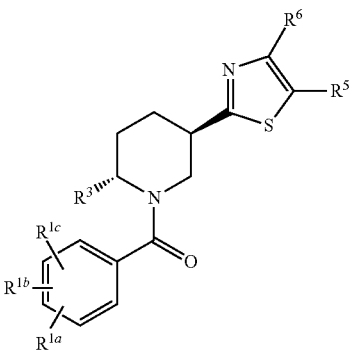

Ie'

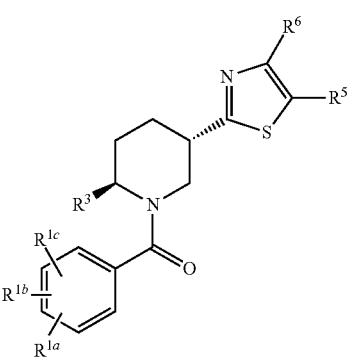

Ie"

wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula If:

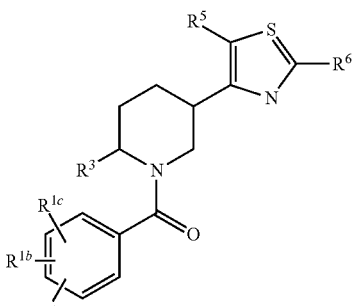

If wherein $R^{1a}$, $R^{1b}$, $R^{1c}$, $R^3$, $R^5$, and $R^6$ are defined herein; or a pharmaceutically acceptable salt thereof.

Embodiments of the present invention include compounds of the formula If' and formula If":

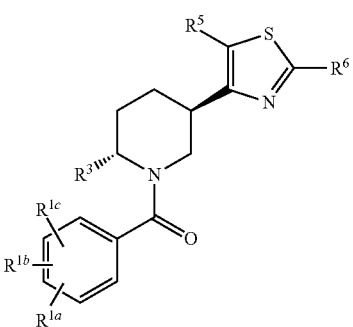

If'

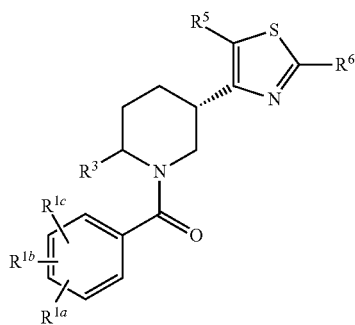

If"

wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Ig:

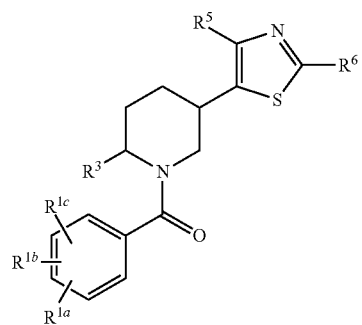

Ig wherein $R^{1a}$, $R^{1b}$, $R^{1c}$, $R^3$, $R^5$, and $R^6$ are defined herein; or a pharmaceutically acceptable salt thereof.

Embodiments of the present invention include compounds of the formula Ig' and formula Ig":

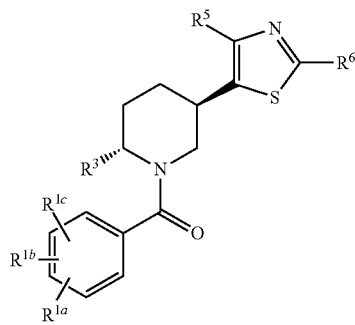

Ig'

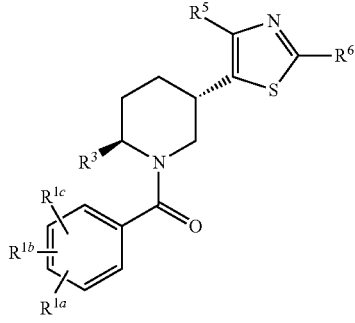

Ig"

wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Ih:

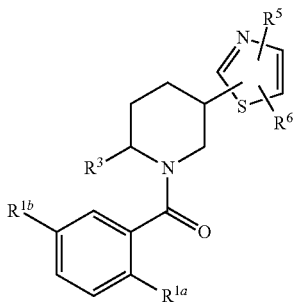

Ih wherein $R^{1a}$, $R^{1b}$, $R^3$, $R^5$, and $R^6$ are defined herein; or a pharmaceutically acceptable salt thereof.

An embodiment of the present invention includes compounds of the formula Ii:

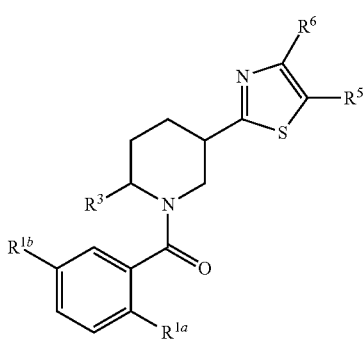

Ii wherein $R^{1a}$, $R^{1b}$, $R^3$, $R^5$, and $R^6$ are defined herein; or a pharmaceutically acceptable salt thereof.

Embodiments of the present invention include compounds of the formula Ii' and formula Ii":

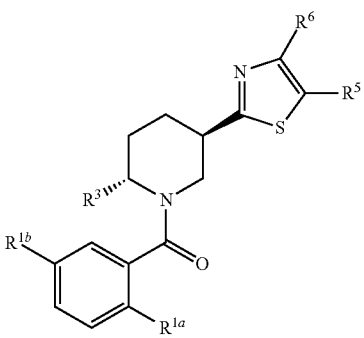

Ii'

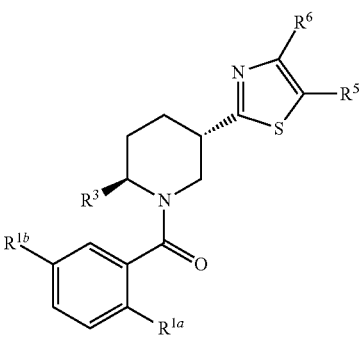

Ii"

wherein $R^{1a}$, $R^{1b}$, $R^3$, $R^5$, and $R^6$ are defined herein; or a pharmaceutically acceptable salt thereof.

An embodiment of the present invention includes compounds of the formula Ij:

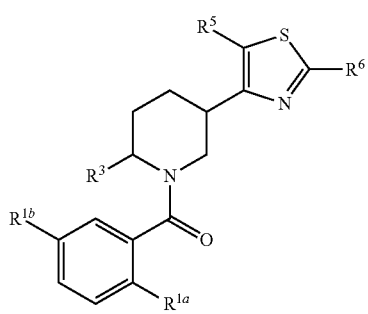
Ij wherein $R^{1a}$, $R^{1b}$, $R^3$, $R^5$, and $R^6$ are defined herein; or a pharmaceutically acceptable salt thereof.

Embodiments of the present invention include compounds of the formula Ij' and formula Ij":

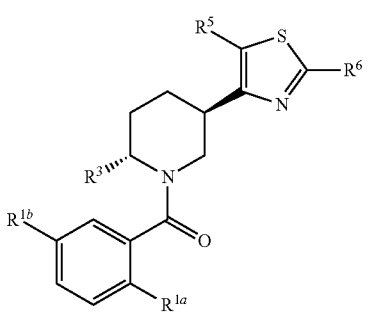
Ij'

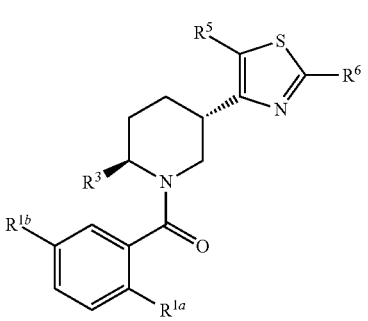
Ij"

wherein $R^{1a}$, $R^{1b}$, $R^3$, $R^5$, and $R^6$ are defined herein; or a pharmaceutically acceptable salt thereof.

An embodiment of the present invention includes compounds of the formula Ik:

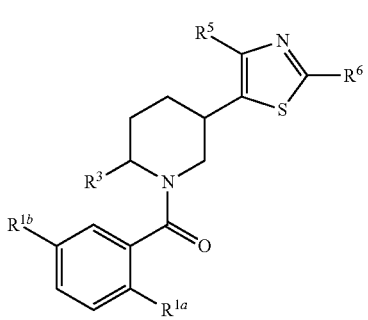
Ik wherein $R^{1a}$, $R^{1b}$, $R^3$, $R^5$, and $R^6$ are defined herein; or a pharmaceutically acceptable salt thereof.

Embodiments of the present invention include compounds of the formula Ik' and formula Ik":

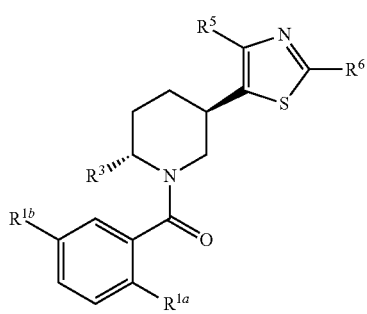
Ik'

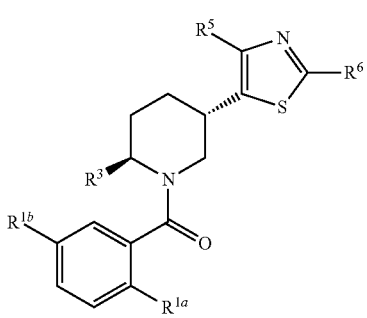
Ik"

wherein $R^{1a}$, $R^{1b}$, $R^3$, $R^5$, and $R^6$ are defined herein; or a pharmaceutically acceptable salt thereof.

An embodiment of the present invention includes compounds of the formula Il:

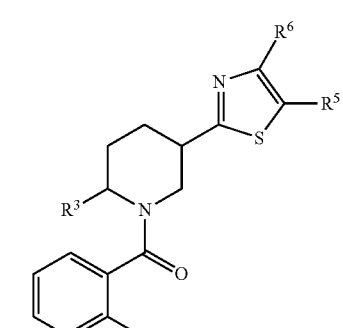
Il wherein $R^{1a}$, $R^3$, $R^5$, and $R^6$ are defined herein; or a pharmaceutically acceptable salt thereof.

An embodiment of the present invention includes compounds of the formula Im:

Im wherein $R^{1a}$, $R^3$, $R^5$, and $R^6$ are defined herein; or a pharmaceutically acceptable salt thereof.

Embodiments of the present invention include compounds of the formula Im' and formula Im":

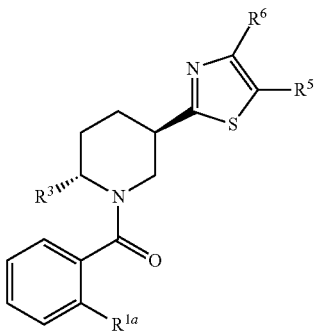

Im'

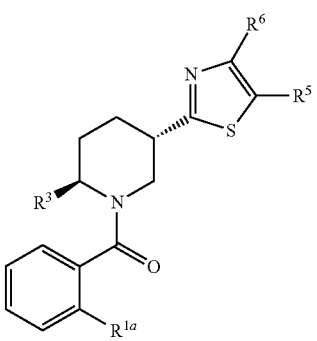

Im"

wherein $R^{1a}$, $R^3$, $R^5$, and $R^6$ are defined herein; or a pharmaceutically acceptable salt thereof.

An embodiment of the present invention includes compounds of the formula In:

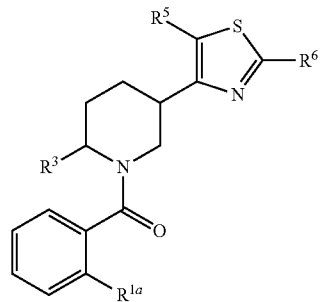

In wherein $R^{1a}$, $R^3$, $R^5$, and $R^6$ are defined herein; or a pharmaceutically acceptable salt thereof.

Embodiments of the present invention include compounds of the formula In' and formula In":

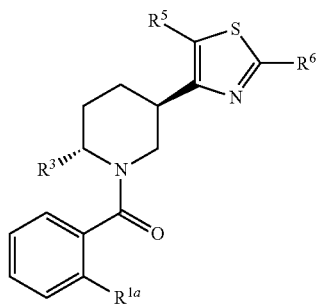

In'

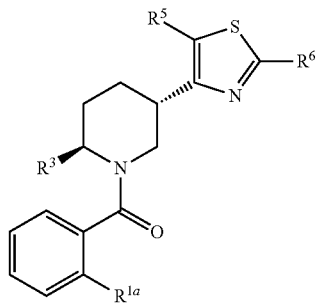

In"

wherein $R^{1a}$, $R^3$, $R^5$, and $R^6$ are defined herein; or a pharmaceutically acceptable salt thereof.

An embodiment of the present invention includes compounds of the formula Io:

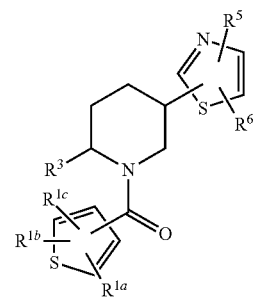

Io wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Ip:

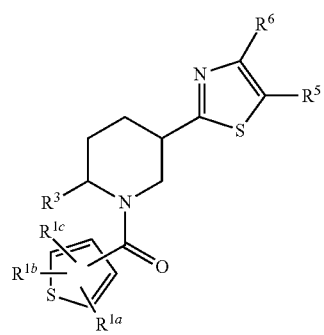

Ip wherein $R^{1a}$, $R^{1b}$, $R^{1c}$, $R^3$, $R^5$, and $R^6$ are defined herein; or a pharmaceutically acceptable salt thereof.

Embodiments of the present invention include compounds of the formula Ip' and formula Ip":

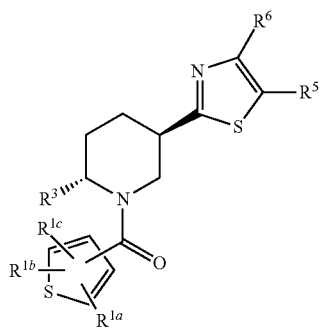

Ip'

-continued

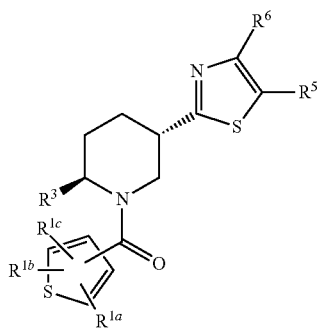
Ip″ wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Iq:

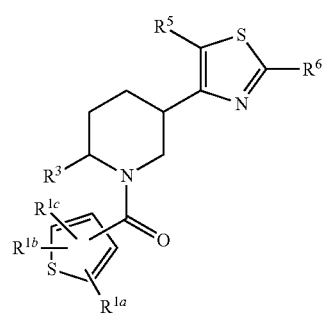
Iq wherein $R^{1a}$, $R^{1b}$, $R^{1c}$, $R^3$, $R^5$, and $R^6$ are defined herein; or a pharmaceutically acceptable salt thereof.

Embodiments of the present invention include compounds of the formula Iq' and formula Iq″:

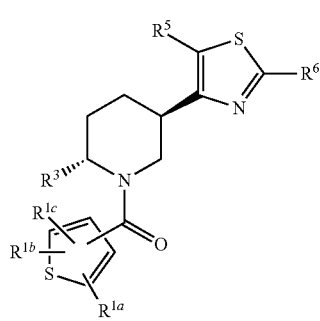
Iq'

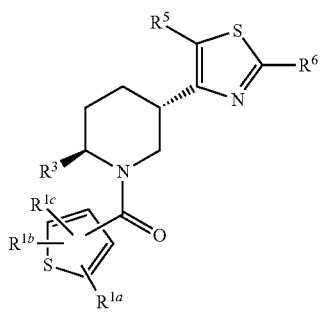
Iq″ wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Ir:

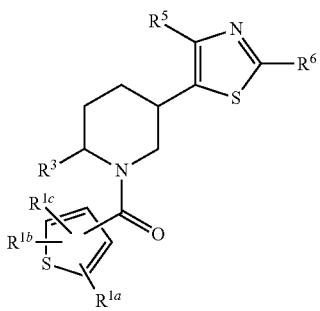
Ir wherein $R^{1a}$, $R^{1b}$, $R^{1c}$, $R^3$, $R^5$, and $R^6$ are defined herein; or a pharmaceutically acceptable salt thereof.

Embodiments of the present invention include compounds of the formula Ir' and formula Ir″:

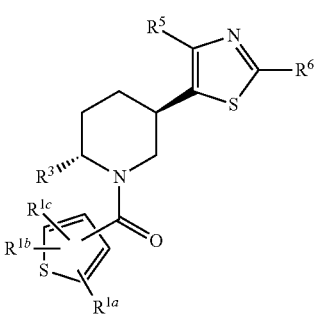
Ir'

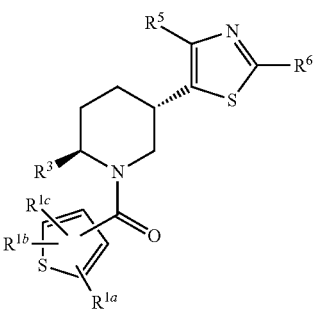
Ir″ wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Is:

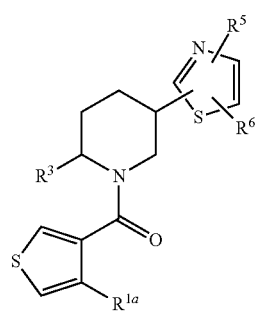
Is wherein $R^{1a}$, $R^3$, $R^5$, and $R^6$ are defined herein; or a pharmaceutically acceptable salt thereof.

An embodiment of the present invention includes compounds of the formula It:

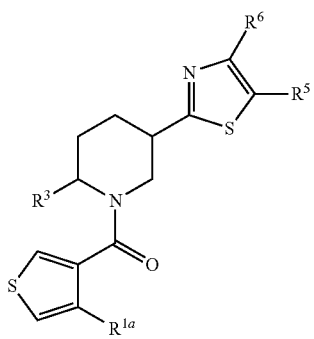

It wherein $R^{1a}$, $R^3$, $R^5$, and $R^6$ are defined herein; or a pharmaceutically acceptable salt thereof.

Embodiments of the present invention include compounds of the formula It' and formula It":

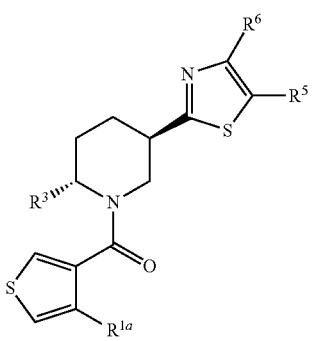

It'

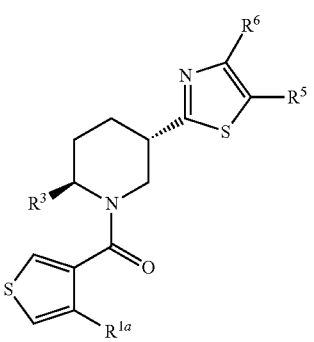

It"

wherein $R^{1a}$, $R^3$, $R^5$, and $R^6$ are defined herein; or a pharmaceutically acceptable salt thereof.

An embodiment of the present invention includes compounds of the formula Iu:

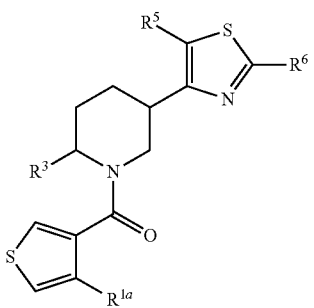

Iu wherein $R^{1a}$, $R^3$, $R^5$, and $R^6$ are defined herein; or a pharmaceutically acceptable salt thereof.

Embodiments of the present invention include compounds of the formula Iu' and formula Iu":

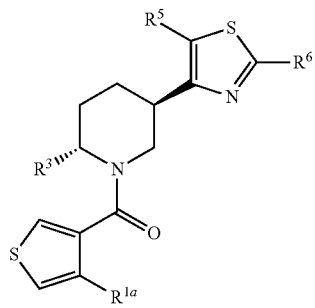

Iu'

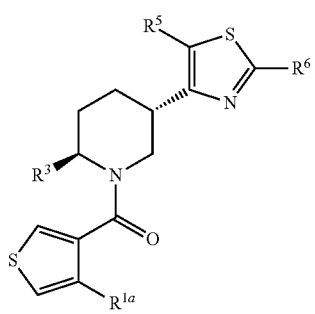

Iu"

wherein $R^{1a}$, $R^3$, $R^5$, and $R^6$ are defined herein; or a pharmaceutically acceptable salt thereof.

An embodiment of the present invention includes compounds of the formula Iv:

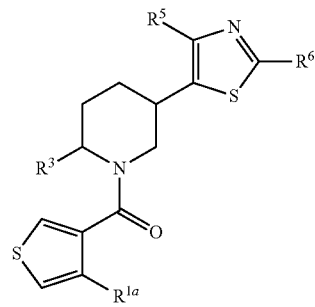

Iv wherein $R^{1a}$, $R^3$, $R^5$, and $R^6$ are defined herein; or a pharmaceutically acceptable salt thereof.

Embodiments of the present invention include compounds of the formula Iv' and formula Iv":

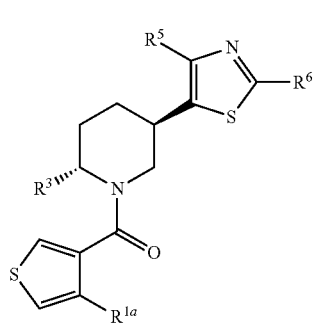

Iv'

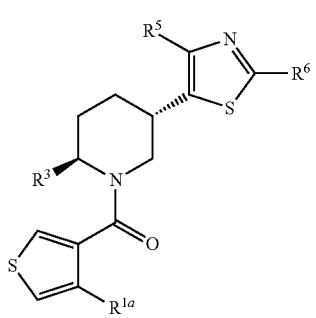

Iv″ wherein $R^{1a}$, $R^3$, $R^5$, and $R^6$ are defined herein; or a pharmaceutically acceptable salt thereof.

An embodiment of the present invention includes compounds of the formula Iw:

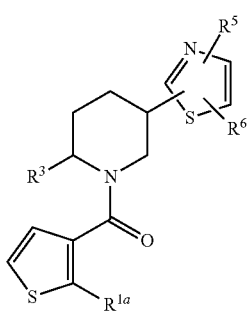

Iw wherein $R^{1a}$, $R^3$, $R^5$, and $R^6$ are defined herein; or a pharmaceutically acceptable salt thereof.

An embodiment of the present invention includes compounds of the formula Ix:

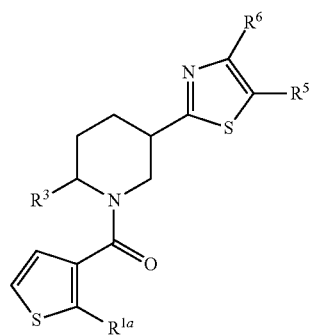

Ix wherein $R^{1a}$, $R^3$, $R^5$, and $R^6$ are defined herein; or a pharmaceutically acceptable salt thereof.

Embodiments of the present invention include compounds of the formula Ix' and formula Ix″:

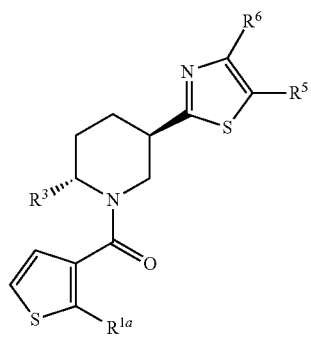

Ix'

Ix″ wherein $R^{1a}$, $R^3$, $R^5$, and $R^6$ are defined herein; or a pharmaceutically acceptable salt thereof.

An embodiment of the present invention includes compounds of the formula Iy:

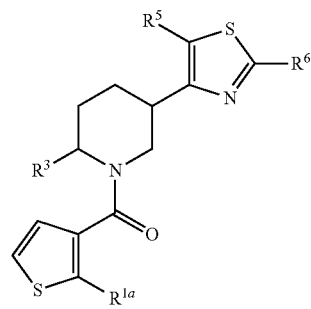

Iy wherein $R^{1a}$, $R^3$, $R^5$, and $R^6$ are defined herein; or a pharmaceutically acceptable salt thereof.

Embodiments of the present invention include compounds of the formula Iy' and formula Iy″:

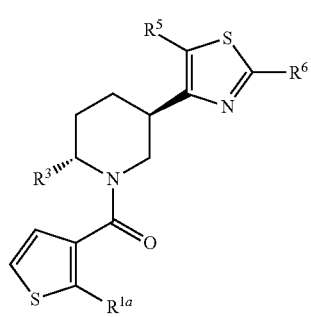

Iy'

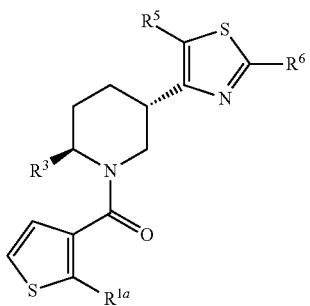

Iy″ wherein $R^{1a}$, $R^3$, $R^5$, and $R^6$ are defined herein; or a pharmaceutically acceptable salt thereof.

An embodiment of the present invention includes compounds of the formula Iz:

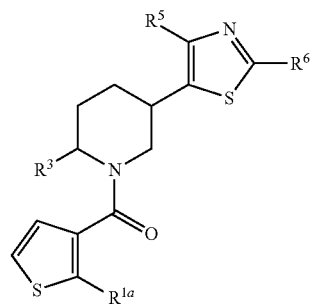

Iz wherein $R^{1a}$, $R^3$, $R^5$, and $R^6$ are defined herein; or a pharmaceutically acceptable salt thereof.

Embodiments of the present invention include compounds of the formula Iz′ and formula Iz″:

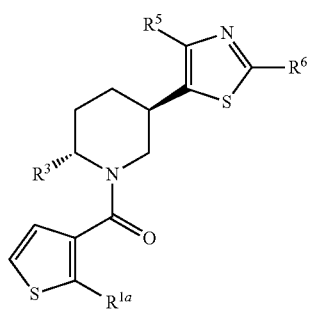

Iz′

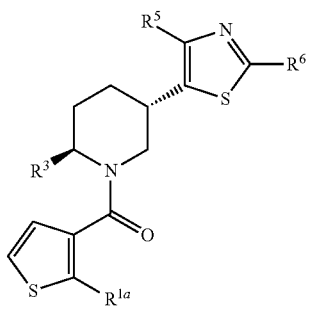

Iz″ wherein $R^{1a}$, $R^3$, $R^5$, and $R^6$ are defined herein; or a pharmaceutically acceptable salt thereof.

An embodiment of the present invention includes compounds of the formula Iaa:

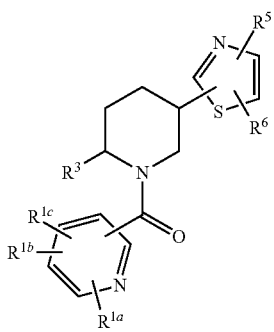

Iaa wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds of the formula Iaa′, Iaa″ and Iaa‴:

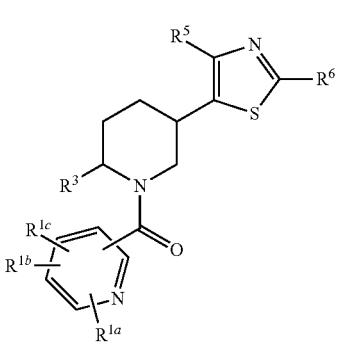

Iaa′

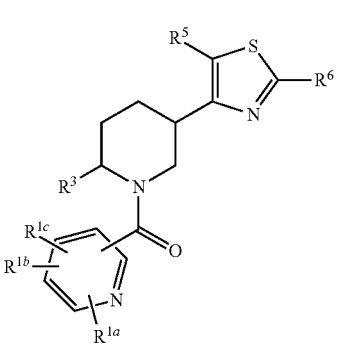

Iaa″

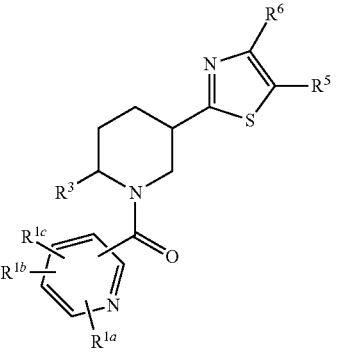

Iaa‴ wherein $R^{1a}$, $R^{1b}$, $R^{1c}$, $R^3$, $R^5$, and $R^6$ are defined herein; or a pharmaceutically acceptable salt thereof.

An embodiment of the present invention includes compounds wherein A is selected from phenyl, pyridyl, thiophenyl, thiazolyl, isothiazolyl, and pyrazolyl. An embodiment of the present invention includes compounds wherein A is selected from phenyl and thiophenyl. An embodiment of the invention includes compounds wherein A is selected from phenyl and 3-thiophenyl. An embodiment of the present invention includes compounds wherein A is phenyl. An embodiment of the present invention includes compounds wherein A is pyridyl. An embodiment of the present invention includes compounds wherein A is thiophenyl. An embodiment of the present invention includes compounds wherein A is 3-thiophenyl. An embodiment of the present invention includes compounds wherein A is thiazolyl. An embodiment of the present invention includes compounds wherein A is isothiazolyl. An embodiment of the present invention includes compounds wherein A is pyrazolyl.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) —(C=O)—O—$C_{1-6}$alkyl, which is unsubstituted or substituted with halogen, hydroxyl or phenyl,
(7) $C_{3-6}$cycloalkyl, which is unsubstituted or substituted with halogen, hydroxyl, or —CN,
(8) heteroaryl, wherein heteroaryl is selected from triazolyl, tetrazolyl, oxazolyl, pyrrolyl, imidazolyl, indolyl, pyridyl, and pyrimidinyl, which is unsubstituted or substituted with halogen, hydroxyl, $C_{1-6}$alkyl, —O—$C_{1-6}$alkyl or —$NO_2$,
(9) phenyl, which is unsubstituted or substituted with halogen, hydroxyl, $C_{1-6}$alkyl, —O—$C_{1-6}$alkyl or —$NO_2$,
(10) —O-phenyl, which is unsubstituted or substituted with halogen, hydroxyl, $C_{1-6}$alkyl, —O—$C_{1-6}$alkyl or —$NO_2$,
(11) —CN,
(12) —$(CH_2)_r$—$S(O)_2$—$C_{1-6}$alkyl, where r is 0, 1 or 2 (wherein if r is 0, a bond is present), and wherein the alkyl is unsubstituted or substituted with halogen or hydroxyl, and
(13) —NH—$C_{1-6}$alkyl, or —N($C_{1-6}$alkyl)($C_{1-6}$alkyl), which is unsubstituted or substituted with halogen, hydroxyl, $C_{1-6}$alkyl, and —O—$C_{1-6}$alkyl.

An embodiment of the present invention includes compounds wherein $R^{1a}$, $R^{1b}$ and $R^{1c}$ are independently selected from the group consisting of:
(1) hydrogen,
(2) halogen,
(3) $C_{1-6}$alkyl, which is unsubstituted or substituted with halogen,
(4) —O—$C_{1-6}$alkyl, which is unsubstituted or substituted with halogen,
(5) —(C=O)—O—$C_{1-6}$alkyl, which is unsubstituted or substituted with halogen, hydroxyl or phenyl,
(6) $C_{3-6}$cycloalkyl, which is unsubstituted or substituted with halogen, hydroxyl, or —CN,
(7) —$(CH_2)_r$—$S(O)_2$—$C_{1-6}$alkyl, where r is 0, 1 or 2 (wherein if r is 0, a bond is present), and wherein the alkyl is unsubstituted or substituted with halogen or hydroxyl, and
(8) heteroaryl, wherein heteroaryl is selected from triazolyl, tetrazolyl, oxazolyl, pyrrolyl, imidazolyl, indolyl, pyridyl, and pyrimidinyl, which is unsubstituted or substituted with halogen, hydroxyl, $C_{1-6}$alkyl, —O—$C_{1-6}$alkyl or —$NO_2$.

An embodiment of the present invention includes compounds wherein $R^{1a}$, $R^{1b}$ and $R^{1c}$ are independently selected from the group consisting of:
(1) hydrogen,
(2) halogen,
(3) —O—$CH_2$—$CH_3$, which is unsubstituted or substituted with halogen,
(4) —(C=O)—O—$C_{1-6}$alkyl, which is unsubstituted or substituted with halogen,
(5) cyclopropyl, which is unsubstituted or substituted with halogen, hydroxyl, or —CN,
(6) —$CH_2$—$S(O)_2$—$C_{1-6}$alkyl, and
(7) heteroaryl, wherein heteroaryl is selected from triazolyl, tetrazolyl, oxazolyl, pyrrolyl, imidazolyl, indolyl, pyridyl, and pyrimidinyl.

An embodiment of the present invention includes compounds wherein $R^{1c}$ is hydrogen, and $R^{1a}$ and $R^{1b}$ are independently selected from the group consisting of:
(1) hydrogen,
(2) fluoro,
(3) —O—$CH_2$—$CHF_2$,
(4) —O—$CH_2$—$CF_3$,
(5) —(C=O)—O—$CH_3$,
(6) cyclopropyl, which is unsubstituted or substituted with CN,
(7) —$CH_2$—$S(O)_2$—$CH_3$, and
(8) heteroaryl, wherein heteroaryl is selected from triazolyl, tetrazolyl, oxazolyl, pyrrolyl, imidazolyl, indolyl, pyridyl, and pyrimidinyl.

An embodiment of the present invention includes compounds wherein $R^{1c}$ is hydrogen, $R^{1b}$ is halogen, and $R^{1a}$ is independently selected from the group consisting of:
(1) triazolyl,
(2) tetrazolyl,
(3) oxazolyl,
(4) pyrrolyl,
(5) imidazolyl,
(6) indolyl,
(7) pyridyl, and
(8) pyrimidinyl.

An embodiment of the present invention includes compounds wherein $R^{1c}$ is hydrogen, $R^{1b}$ is hydrogen, and $R^{1a}$ is independently selected from the group consisting of:
(1) triazolyl,
(2) tetrazolyl,
(3) oxazolyl,
(4) pyrrolyl,
(5) imidazolyl,
(6) indolyl,
(7) pyridyl, and
(8) pyrimidinyl.

An embodiment of the present invention includes compounds wherein $R^{1c}$ is hydrogen, $R^{1b}$ is halogen, and $R^{1a}$ is independently selected from the group consisting of:
(1) triazolyl,
(2) tetrazolyl, and
(3) pyrimidinyl.

An embodiment of the present invention includes compounds wherein $R^{1c}$ is hydrogen, $R^{1b}$ is fluoro, and $R^{1a}$ is independently selected from the group consisting of:
(1) triazolyl,
(2) tetrazolyl, and
(3) pyrimidinyl.

An embodiment of the present invention includes compounds wherein $R^{1c}$ is hydrogen, $R^{1b}$ is hydrogen, and $R^{1a}$ is independently selected from the group consisting of:
(1) triazolyl,
(2) tetrazolyl, and
(3) pyrimidinyl.

In a further embodiment, $R^{1a}$ is triazolyl. In another embodiment, $R^{1a}$ is tetrazolyl. In a still further embodiment, $R^{1a}$ is pyrimidinyl.

An embodiment of the present invention includes compounds wherein $R^3$ is $C_{1-6}$alkyl. An embodiment of the present invention includes compounds wherein $R^3$ is $C_{3-6}$cycloalkyl. An embodiment of the present invention includes compounds wherein $R^3$ is methyl or ethyl. An embodiment of the present invention includes compounds wherein $R^3$ is methyl. An embodiment of the present invention includes compounds wherein $R^3$ is (R)-methyl. An embodiment of the present invention includes compounds wherein $R^5$ and $R^6$ are independently selected from the group consisting of:
(1) hydrogen,
(2) halogen,
(3) $C_{1-6}$alkyl, which is unsubstituted or substituted with halogen, hydroxyl, —O—$C_{1-6}$alkyl,
(4) —(C=O)O—$C_{1-6}$alkyl, which is unsubstituted or substituted with halogen, hydroxyl or phenyl
(5) —CN,
(6) —(C=O)NH($C_{1-6}$alkyl), and
(7) —(C=O)N($C_{1-6}$alkyl)($C_{1-6}$alkyl).

An embodiment of the present invention includes compounds wherein $R^5$ and $R^6$ are independently selected from the group consisting of:
(1) hydrogen,
(2) halogen,
(3) $C_{1-6}$alkyl,
(4) trifluoromethyl,
(5) $CHF_2$,
(6) —(C=O)O—$C_{1-6}$alkyl, and (7) 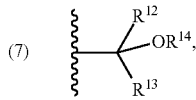

wherein $R^{12}$ and $R^{13}$ are independently hydrogen or $C_{1-2}$alkyl (optionally substituted with fluoro), and $R^{14}$ is hydrogen or $C_{1-6}$alkyl.

An embodiment of the present invention includes compounds wherein $R^5$ and $R^6$ are independently selected from the group consisting of:
(1) hydrogen,
(2) methyl,
(3) ethyl,
(4) trifluoromethyl,
(5) $CHF_2$,
(6) —(C=O)O-ethyl, and (7) 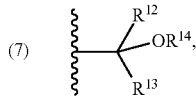

wherein $R^{12}$ and $R^{13}$ are independently hydrogen, methyl, —$CHF_2$ or $CF_3$.

An embodiment of the present invention includes compounds wherein $R^5$ is selected from hydrogen or methyl. A further embodiment includes compounds wherein $R^5$ is hydrogen. Another embodiment includes compounds wherein $R^5$ is methyl.

An embodiment of the present invention compounds wherein $R^6$ is

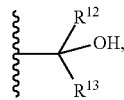

where $R^{12}$ and $R^{13}$ are independently hydrogen, methyl, —$CHF_2$ or $CF_3$. In a further embodiment, $R^{12}$ and $R^{13}$ are both methyl.

An embodiment of the present invention includes compounds wherein $R^5$ is hydrogen, and $R^6$ is

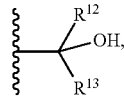

wherein $R^{12}$ and $R^{13}$ are independently hydrogen, methyl, —$CHF_2$ or $CF_3$. In a further embodiment, $R^{12}$ and $R^{13}$ are both methyl.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. For example, formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The present invention also includes all pharmaceutically acceptable isotopic variations of a compound of formula I in which one or more atoms is replaced by atoms having the same atomic number but an atomic mass or mass number different from the atomic mass or mass number usually found in nature. Examples of isotopes suitable for inclusion in the compounds of the invention include isotopes of hydrogen (such as $^2$H and $^3$H), carbon (such as $^{11}$C, $^{13}$C and $^{14}$C), nitrogen (such as $^{13}$N and $^{15}$N), oxygen (such as $^{15}$O, $^{17}$O and $^{18}$O), phosphorus (such as $^{32}$P), sulfur (such as $^{35}$S), fluorine (such as $^{18}$F), iodine (such as $^{123}$I and $^{125}$I) and chlorine (such as $^{36}$Cl). Certain isotopically-labelled compounds of Formula I, for example those incorporating a radioactive isotope, are useful in drug and/or substrate tissue distribution studies. The radioactive isotopes tritium, i.e. 3H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labeled reagent previously employed.

As used herein, "alkyl" is intended to include both branched- and straight-chain saturated aliphatic hydrocarbon groups having the specified number of carbon atoms. For example, "$C_1$-$C_6$" or "$C_{1-6}$," as in "$C_1$-$C_6$alkyl" or "$C_{1-6}$alkyl," is defined to include groups having 1, 2, 3, 4, 5, or 6 carbons in a linear or branched arrangement. $C_{1-6}$ alkyl includes all of the hexyl alkyl and pentyl alkyl isomers, as well as n-, iso-, sec- and t-butyl, n- and isopropyl, ethyl and methyl. As another example, $C_{1-4}$ alkyl means n-, iso-, sec- and t-butyl, n- and isopropyl, ethyl and methyl. Commonly used abbreviations for alkyl groups may be used throughout the specification, e.g. methyl may be represented by conventional abbreviations including "Me" or $CH_3$ or a symbol that is an extended bond without defined terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkenyl" refers to a non-aromatic hydrocarbon radical, straight or branched, containing at least 1 carbon-to-carbon double bond. Preferably, one carbon-to-carbon double bond is present, and up to 4 non-aromatic carbon-carbon double bonds may be present. As an example, "$C_3$-$C_6$ alkenyl" or "$C_{3-6}$ alkenyl" means an alkenyl radical having from 3 to 6 carbon atoms. Alkenyl groups include ethenyl, propenyl, butenyl and cyclohexenyl. The straight, branched or cyclic portion of the alkenyl group may contain double bonds and may be substituted if a substituted alkenyl group is indicated.

The term "alkynyl" refers to a hydrocarbon radical, straight or branched, containing at least one carbon-to-carbon triple bond. Up to 3 carbon-carbon triple bonds may be present. As an example, "$C_3$-$C_6$ alkynyl" or "$C_{3-6}$ alkynyl" means an alkynyl radical having from 3 to 6 carbon atoms. Alkynyl groups include ethynyl, propynyl and butynyl. The straight or branched portion of the alkynyl group may contain triple bonds and may be substituted if a substituted alkynyl group is indicated.

The term "heterocycle," as used herein, includes both unsaturated and saturated heterocyclic moieties, wherein the unsaturated heterocyclic moieties (i.e. "heteroaryl") include, for example, benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl (pyrimidinyl), pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

As appreciated by those of skill in the art, halogen or halo as used herein is intended to include fluoro, chloro, bromo and iodo. The term "trifluoromethyl" refers to the group (—$CF_3$).

A group which is designated as being independently substituted with substituents may be independently substituted with multiple numbers of such substituents.

The term "pharmaceutically acceptable salts" refers to salts prepared from pharmaceutically acceptable non-toxic bases or acids, including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound selected from the group consisting of the compounds disclosed in the following Examples, pharmaceutically acceptable salts thereof and individual enantiomers or diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals may be treated according to the method of the present invention. The present invention is directed to a compound of the present invention or a pharmaceutically acceptable salt thereof that could be useful in medicine. The present invention may further be directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., *Biochem. Biophys. Res. Comm.* 2001, 280:976-981). Briefly, for intracellular calcium measurements, Chinese hamster ovary (CHO) cells expressing the orexin-1 receptor (e.g., rat or human) or the orexin-2 receptor (e.g., rat or human), are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at approximately 20,000 cells per well into 384-well clear bottom sterile plates coated with poly-D-lysine. The seeded plates are incubated overnight at 37° C. and 5% $CO_2$. Human ala-6,12 orexin-A can be used as the agonist and prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then in assay buffer. On the day of the assay, cells are washed 3 times with 100 µl assay buffer and then incubated for 60 minutes (37° C., 5% $CO_2$) in 60 µl assay buffer containing 1 µM Fluo-4 AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 µl, incubated for 5 minutes, and then 25 µl of agonist is added. Fluorescence is measured for each well at 1 second intervals for 5 minutes, and the height of each fluorescence peak is compared to the height of the fluorescence peak induced by 70 pM of agonist ala-6,12 orexin-A with buffer in place of test compound. $IC_{50}$ value for the test compound is determined to be the concentration of compound needed to inhibit 50% of the agonist response. Alternatively, compound potency can be assessed using a radioligand binding assay (described in Bergman et. al., *Bioorg. Med. Chem. Lett.* 2008, 18:1425-1430) in which the inhibition constant (Ki) is determined in membranes prepared from CHO cells expressing either the OX1 or OX2 receptor. The intrinsic orexin receptor antagonist activity of a compound of the present invention may be determined by these assays.

All of the final compounds of the following Examples had activity in antagonizing the orexin-2 receptor in one or both of the described assays. The Example compounds were tested for activity in the FLIPR assay against the human orexin-2 receptor, each having an inflection point (IP) of between about 5 nM and 3000 nM. A majority of the compounds of the Examples had activity in antagonizing the human orexin-2 receptor in the FLIPR assay with an IP of about 5 nM to 50 nM. Additional data is provided in the following Examples. Additional data is provided in the following Examples. The assay results provided infra (see Table 7) is indicative of the intrinsic activity of the Example compounds for use as antagonists of the orexin-1 receptor and/or the orexin-2 receptor. In general, one of ordinary skill in the art would appreciate that a substance is considered to effectively antagonize the orexin receptor if it has an IC50 of less than about 50 µM, preferably less than about 100 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances and/or sleep problems (such as excessive daytime sleepiness/drowsiness, idiopathic insomnia, insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, sleep walking and enuresis, sleep disorders which accompany aging); Alzheimer's sundowning; conditions associated with circadian rhythmicity, including mental and physical disorders associated with travel across time zones and with rotating shift-work schedules; conditions due to drugs which cause reductions in REM sleep as a side effect; fibromyalgia; syndromes which are manifested by non-restorative sleep; muscle pain or sleep apnea associated with respiratory disturbances during sleep; conditions which result from a diminished quality of sleep; eating disorders, including those associated with excessive food intake and complications associated therewith, compulsive eating disorders, obesity (due to any cause, whether genetic or environmental), obesity-related disorders, anorexia, bulimia, cachexia, dysregulated appetite control; hypertension; diabetes; elevated plasma insulin concentrations and insulin resistance; dyslipidemias; hyperlipidemia; endometrial, breast, prostate and colon cancer; osteoarthritis; cholelithiasis; gallstones; heart disease; lung disease; abnormal heart rhythms and arrhythmias; myocardial infarction; congestive heart failure; coronary heart disease; acute and congestive heart failure; hypotension; hypertension; urinary retention; osteoporosis; angina pectoris; myocardial infarction; ischemic or haemorrhagic stroke; subarachnoid haemorrhage; ulcers; allergies; benign prostatic hypertrophy; chronic renal failure; renal disease; impaired glucose tolerance; sudden death; polycystic ovary disease; craniopharyngioma; Prader-Willi Syndrome; Frohlich's syndrome; GH-deficient subjects; normal variant short stature; Turner's syndrome; pathological conditions showing reduced metabolic activity or a decrease in resting energy expenditure as a percentage of total fat-free mass, e.g. children with acute lymphoblastic leukemia; metabolic syndrome, also known as syndrome X; insulin resistance syndrome; reproductive hormone abnormalities; sexual and reproductive dysfunction, such as impaired fertility, infertility, hypogonadism in males and hirsutism in females; fetal defects associated with maternal obesity; gastrointestinal motility disorders; intestinal motility dyskinesias; obesity-related gastro-esophageal reflux; hypothalmic diseases; hypophysis diseases; respiratory disorders, such as obesity-hypoventilation syndrome (Pickwickian syndrome), breathlessness; cardiovascular disorders; inflammation, such as systemic inflammation of the vasculature; arteriosclerosis; hypercholesterolemia; hyperuricaemia; lower back pain; gallbladder disease, gout; kidney cancer; increased anesthetic risk; diseases or disorders where abnormal oscillatory activity occurs in the brain, including migraine, neuropathic pain, Parkinson's disease, psychosis and schizophrenia, as well as diseases or disorders where there is abnormal coupling of activity, particularly through the thalamus; cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; hot flashes; night sweats; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; congestive heart failure; conditions of the genital/urinary system; disorders of sexual function; inadequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric dyskinesia; gastric ulcers; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium; amnestic disorders or age related cognitive decline; psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, including substance use, substance abuse, substance seeking, substance reinstatement, all types of psychological and physical addictions and addictive behaviors, reward-related behaviors (including substance-induced persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification); chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor); epilepsy; dyskinesias, including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), restless leg syndrome and dystonia (including generalized dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; conditions associated with visceral pain such as irritable bowel syndrome, and angina; trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; increasing satisfaction with the intensity of sleep; increasing sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing the time spent awake following the initial onset of sleep; increasing the total amount of sleep; reduce the fragmentation of sleep; altering the timing, frequency or duration of REM sleep bouts; altering the timing, frequency or duration of slow wave (i.e. stages 3 or 4) sleep bouts; promoting slow wave sleep; enhancing EEG-delta activity during sleep; decreasing nocturnal arousals, especially early morning awakenings; increasing daytime alertness; reducing daytime drowsiness; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; reducing the risk of secondary outcomes of obesity, such as reducing the risk of left ventricular hypertrophy; treating or controlling diabetes and appetite, taste, eating, or drinking disorders; treating or controlling hypothalamic diseases; increasing learning; augmenting memory; increasing retention of memory; enhancing memory; increasing immune response; increasing immune function; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian patient in need thereof which comprises administering to the patient a therapeutically effective amount of a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied; however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends on the desired therapeutic effect, the route of administration, and the duration of the treatment. The dose will vary from patient to patient depending upon the nature and severity of disease, the patient's weight, special diets then being followed by a patient, concurrent medication, and other factors that those skilled in the art will recognize. Generally, dosage levels of between 0.0001 to 10 mg/kg of body weight daily are administered to the patient, e.g., humans and elderly humans, to obtain effective antagonism of orexin receptors. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day.

Pharmaceutical compositions of the present invention may be provided in a solid dosage formulation, such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 mg of the active ingredient, such as 1, 5, 10, 15, 20, 25, 50, 75, 100, 150, 200, 250, 300, 400, 500, 600, 750, 800, 900, and 1000 mg of the active ingredient for the symptomatic adjustment of the dosage to the patient to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, omortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: (a) insulin sensitizers including PPARγ antagonists (such as glitazones (e.g. ciglitazone; darglitazone; englitazone; isaglitazone (MCC-555); pioglitazone; rosiglitazone; troglitazone; BRL49653; CLX-0921; 5-BTZD), GW-0207, LG-100641, and LY-300512, and the like); (b) biguanides such as metformin and phenformin; (c) insulin or insulin mimetics, such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (d) sulfonylureas, such as acetohexamide, chlorpropamide, diabinese, glibenclamide, glipizide, glyburide, glimepiride, gliclazide, glipentide, gliquidone, glisolamide, tolazamide and tolbutamide; (e) α-glucosidase inhibitors, such as acarbose, adiposine, camiglibose, emiglitate, miglitol, voglibose, pradimicin-Q, salbostatin, CKD-711, MDL-25,637, MDL-73,945 and MOR 14, and the like; (f) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants (such as cholestyramine, colestipol, dialkylaminoalkyl derivatives of a cross-linked dextran; Colestid®; LoCholest®, and the like), (iii) nicotinyl alcohol, nicotinic acid or a salt thereof, (iv) proliferator-activator receptor a agonists (such as fenofibric acid derivatives, such as gemfibrozil, clofibrate, fenofibrate and benzafibrate), (v) inhibitors of cholesterol absorption (such as stanol esters, beta-sitosterol, sterol glycosides such as tiqueside, azetidinones such as ezetimibe, and acyl CoA:cholesterol acyltransferase (ACAT)) inhibitors such as avasimibe and melinamide, (vi) anti-oxidants (such as probucol), (vii) vitamin E, and (viii) thyromimetics; (g) PPARα agonists such as beclofibrate, benzafibrate, ciprofibrate, clofibrate, etofibrate, fenofibrate and gemfibrozil, and other fibric acid derivatives, such as Atromid®, Lopid® and Tricor®, and the like, and PPARα agonists as described in PCT Patent Application Publication No. WO 97/36579; (h) PPARδ agonists, such as those disclosed in PCT Patent Application Publication No. WO97/28149; (i) PPAR α/δ agonists, such as muraglitazar, and the compounds disclosed in U.S. Pat. No. 6,414,002; (j) anti-obesity agents, such as (l) growth hormone secretagogues, growth hormone secretagogue receptor agonists/antagonists, such as NN703, hexarelin, MK-0677, SM-130686, CP-424,391, L-692,429, and L-163, 255, and such as those disclosed in U.S. Pat. Nos. 5,536,716, and 6,358,951, U.S. Patent Application Nos. 2002/049196 and 2002/022637, and PCT Patent Application Publication Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Patent Application Publications Nos. WO 96/33159, WO 98/33765, WO98/43636, WO098/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Patent Application Publication No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Application Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180, 653; 6,191,160; 6,313,298; 6,335,345; 6,337,332; 6,326, 375; 6,329,395; 6,340,683; 6,388,077; 6,462,053; 6,649, 624; and 6,723,847, European Patent Nos. EP 01010691, and EP 01044970; and PCT Patent Application Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175 (9) melanin-concentrating hormone (MCH) receptor antagonists, such as those disclosed in PCT Patent Application Publication Nos WO 01/21577 and WO 01/21169; (10) melanin-concentrating hormone 1 receptor (MCH1R) antagonists, such as T-226296 (Takeda), and those disclosed in PCT Patent Application Publication Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Patent Application Publication Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl) carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Patent Application Publication Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387, 595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically accepbtle salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically accepbtle salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2001/68609, WO2004/085403, WO2005/118548, WO2008/147518, WO2009/143033 and WO2010/048012) or as illustrated herein. The following abbreviations are used herein: Me: methyl; Et: ethyl; t-Bu: tert-butyl; Ar: aryl; Ph: phenyl; Bn: benzyl; Ac: acetyl; Boc: tert-butyloxy carbonyl; BSA: bovine serum albumin; CsF: caesium fluoride; DCM: dichloromethane; DIPEA: N,N-diisopropylethylamine; DMA: dimethylacetamide; DMF: N,N-dimethylformamide; DMSO: dimethylsulfoxide; EtOAc: ethylacetate; EtOH: ethanol; FmocOSu: N-(9-Fluorenylmethoxycarbonyloxy)succinimide; HATU: (O-(7-azabenzotriazol-1-yl)-N,N,N',N'-tetramethyluronium hexafluorophosphate); HCl: hydrogen chloride; HPLC: high performance liquid chromatography; i-PrMgCl: isopropylmagnesium chloride; Lawesson's reagent: 2,4-bis(4-methoxyphenyl)-1,3,2,4-dithiadiphosphetane-2,4-disulfide; LiAlH4: Lithium aluminium hydride; LDA: Lithium diisopropylamide; LiOH: lithium hydroxide; MeOH: methanol; MgSO$_4$: magnesium sulfate; NaClO$_2$: sodium chlorite; NaOH: sodium hydroxide; NaI sodium iodide: Na$_2$SO$_4$: sodium sulfate; rt: room temperature; NBS: N-Bromosuccinimide; NH$_4$Cl: ammonium chloride; SOCl$_2$: thionyl chloride; T$_3$P: 2,4,6-tripropyl-1,3,5,2,4,6-trioxatriphosphorinane-2,4,6-trioxide; TEA: triethylamine; TEMPO: (2,2,6,6-tetramethylpiperidin-1-yl)oxidanyl; THF: tetrahydrofuran; TFA: trifluoracetic acid. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLES

The following general synthetic schemes are useful for preparation of intermediates and reagents that can be used in the preparation of the compounds of the invention.

Intermediate A: Preparation of 2-(1-Cyanocyclopropyl)benzoic acid

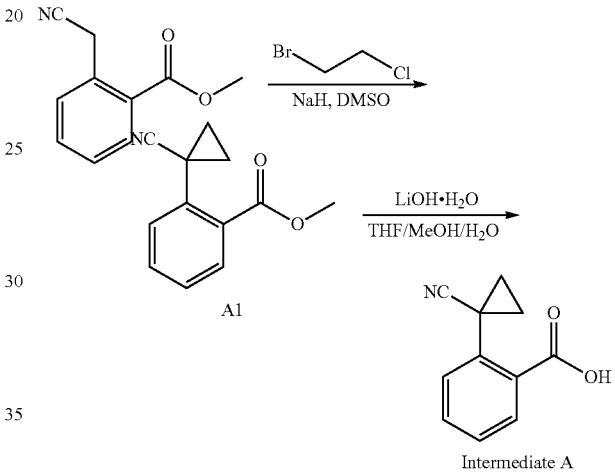

Step 1: Methyl 2-(1-cyanocyclopropyl)benzoate (A1)

To a solution of NaH (1.1 g, 26.2 mmol) in DMSO (20 mL) was added methyl 2-(cyanomethyl)benzoate (2 g, 11.4 mmol); after stirring at RT under nitrogen for 1 h, 1-bromo-2-chloroethane (1.8 g, 12.6 mmol) was added and the mixture stirred at RT for 2 h. The mixture was quenched with ice water (10 mL) and extracted with EtOAc (10 mL×3). The organic layers were combined, dried over Na$_2$SO$_4$ and concentrated in vacuo to give the crude compound, which was purified by column chromatography on silica gel (petroleum ether/EtOAc 20:1) to give the title compound as a white solid. MS (ESI) m/e (M+H+) detected.

Step 2: 2-(1-Cyanocyclopropyl)benzoic acid (Intermediate A)

To a solution of the product from step 1 in THF/MeOH/H$_2$O (3:1:1, 16 mL) was added lithium hydroxide in water (3 mL) and the mixture stirred overnight at RT. The THF and MeOH were removed in vacua and the resulting solution acidified to pH~1 with HCl (1 N) to give a white crystalline precipitate. The solid was isolated by filtration, washed with water and dried in vacuo to afford Intermediate A as a white solid. MS (ESI) m/e (M+H$^+$): 187.9.

Intermediate B: Preparation of 4-(Pyrimidin-2-yl)thiophene-3-carboxylic acid

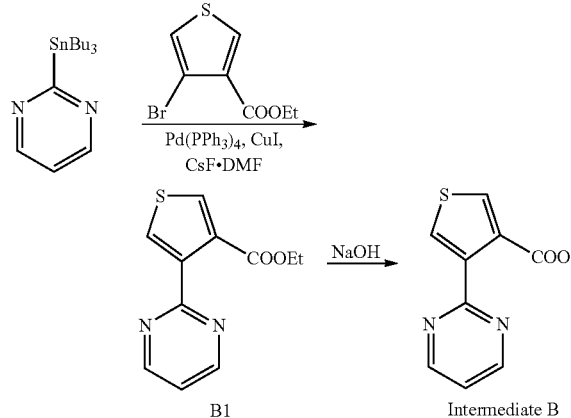

B1      Intermediate B

Step 1: 4-Pyrimidin-2-yl-thiophene-3-carboxylic acid ethyl ester (B1)

To a degassed solution of 4-bromothiophene-3-carboxylic acid ethyl ester (1 g, 4.3 mmol), 2-tributylstannanylpyrimidine (1.587 g, 4.3 mmol) and CsF (1.3 g, 8.6 mmol) in DMF (5 mL) was added Pd(PPh$_3$)$_4$ (0.5 g, 0.43 mmol) and CuI (0.16 g, 0.86 mmol). The mixture was heated under microwave conditions at 110° C. for 45 minutes, cooled and diluted with sat NH$_4$Cl solution and water. The mixture was extracted with EtOAc (20 mL×5) and the combined organic layers dried over Na$_2$SO$_4$, filtered and the filtrate concentrated in vacuo. The residue was purified by chromatography on silica gel (petroleum ether: EtOAc=10:1) to provide the title compound as yellow oil. LRMS m/z (M+H) 235.0 found, 235.0 required.

Step 2: 4-Pyrimidin-2-yl-thiophene-3-carboxylic acid (Intermediate B)

The title compound was prepared from the product of step 1 using the procedure described for the synthesis of compound F2. LRMS m/z (M+H) 207.0 found, 207.0 required.

Intermediate C: Preparation of 2-(2H-Tetrazol-2-yl)benzoic acid

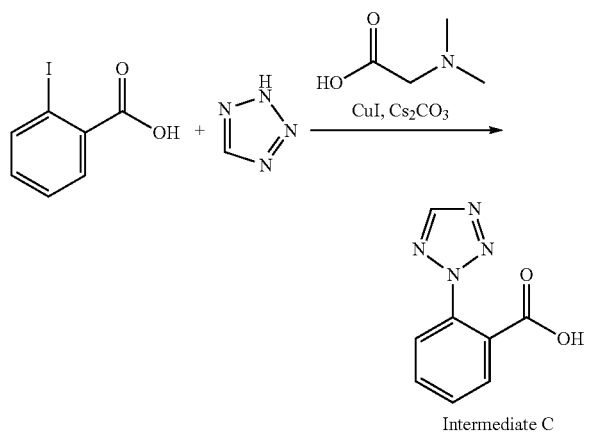

Intermediate C

To a 20 mL microwave tube was charged 2-iodobenzoic acid (1.85 g, 7.46 mmol), cesium carbonate (4.06 g, 12.5 mmol), copper(I) iodide (0.128 g, 0.671 mmol), and DMA (8.0 mL). N,N-Dimethylglyine (0.131 g, 1.27 mmol) and tetrazole (1.29 g, 18.4 mmol) were added, and the solution irradiated in a microwave reactor at 100° C. for 1 hour. The reaction mixture was diluted with water and 1 N aqueous sodium hydroxide and washed with EtOAc. The aqueous fraction was acidified with conc. HCl and extracted 2× with EtOAc. The combined organic fractions were washed with brine, dried over MgSO$_4$, filtered, and concentrated in vacuo. The residue was purified by silica gel chromatography [0-85% (1% acetic acid in EtOAc) in hexanes], to provide the title compound. $^1$H NMR (400 MHz, CD$_3$OD): δ 7.72-7.84 (m, 3H), 8.07 (dd, J=7.6, 1.6 Hz, 1H), 8.90 (s, 1H) ppm. LRMS m/z (M+H) 191.1 found, 191.2.

Intermediate D: Preparation of 2-(2H)-1,2,3-Triazol-2-yl)thiophene-3-carboxylic acid

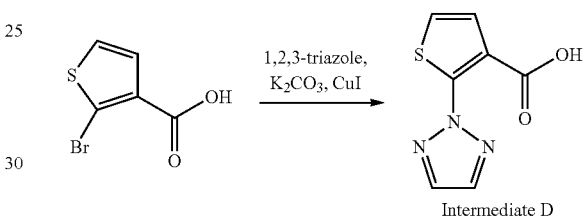

Intermediate D

A solution of 2-bromo-3-thiophene carboxylic acid (1.50 g, 7.24 mmol), 1H-1,2,3-triazole (0.600 g, 8.69 mmol), potassium carbonate (2.00 g, 14.5 mmol), and copper iodide (0.138 g, 0.724 mmol) in DMF (36.2 mL) was sparged with nitrogen and heated to 75° C. for 96 h. The cooled reaction mixture was diluted with water, washed with ether, and acidified with conc. HCl. The acidic aqueous solution was extracted 3× with EtOAc and the combined organic fractions washed with brine, dried over MgSO$_4$, filtered, and concentrated in vacuo. The crude material was purified by silica gel chromatography [0-70% (1% acetic acid in EtOAc) in hexanes], to provide the title compound as an off-white solid. LRMS m/z (M+H) 196.2 found, 196.1 required.

Intermediate E: Preparation of potassium 2-(pyrimidin-2-yl)thiophene-3-carboxylate

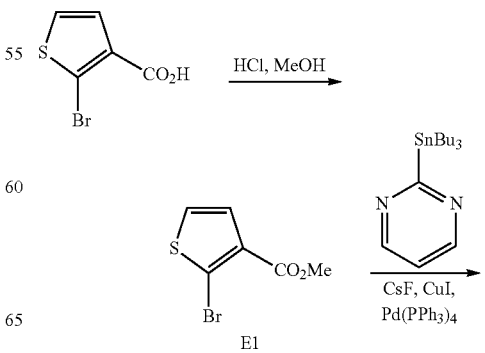

E1

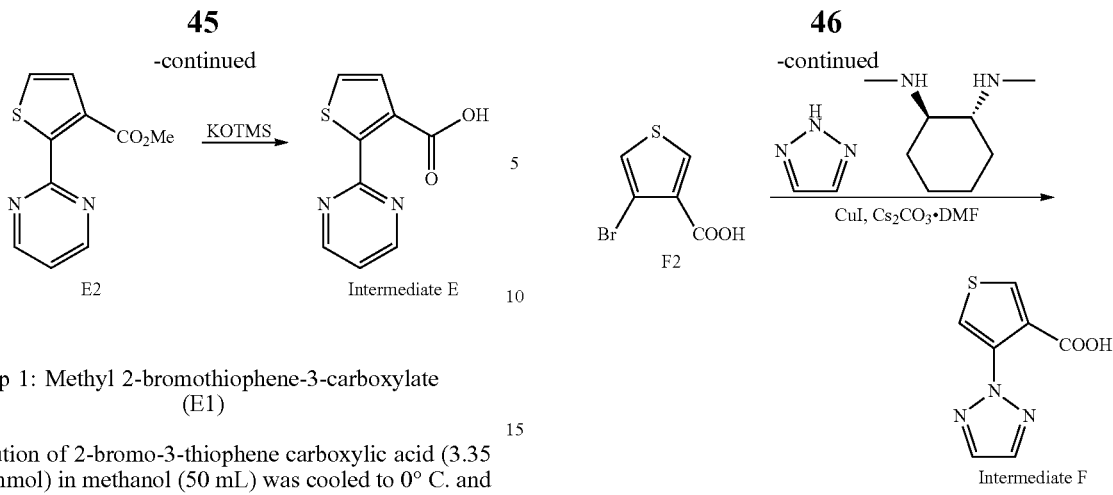

Step 1: Methyl 2-bromothiophene-3-carboxylate (E1)

A solution of 2-bromo-3-thiophene carboxylic acid (3.35 g, 16.2 mmol) in methanol (50 mL) was cooled to 0° C. and saturated with gaseous HCl. The solution was heated to 60° C. overnight, cooled and then concentrated in vacuo. The residue was redissolved in EtOAc, washed with saturated aqueous sodium bicarbonate and brine, dried over $Na_2SO_4$, filtered, and concentrated in vacuo, providing methyl 2-bromothiophene-3-carboxylate as yellow oil. LRMS m/z (M+H) 221.1 found, 221.0 required.

Step 2: Methyl 2-(pyrimidin-2-yl)thiophene-3-carboxylate (E2)

A solution of the product from step 1 (1.74 g, 7.87 mmol), 2-(tributylstannyl)pyrimidine (4.36 g, 11.81 mmol), CsF (4.78 g, 31.5 mmol), and copper(I) iodide (0.450 g, 2.36 mmol) in DMF (16 mL) in a pressure vessel was sparged with nitrogen and treated with $Pd(PPh_3)_4$ (0.455 g, 0.394 mmol). The mixture was sealed and heated at 120° C. overnight. The cooled reaction mixture was partitioned between EtOAc and water and filtered through celite. The organic layer was washed with saturated aqueous sodium bicarbonate and brine, dried over $MgSO_4$, filtered, and concentrated in vacuo. The residue was purified by silica gel chromatography (0-30% EtOAc in hexanes), to provide the title compound as a yellow solid. LRMS m/z (M+H) 221.2 found, 221.1 required.

Step 3: Potassium 2-(pyrimidin-2-yl)thiophene-3-carboxylate (Intermediate E)

A solution of the product from step 2 (0.695 g, 3.16 mmol) and potassium trimethylsilanolate (0.506 g, 3.94 mmol) in THF (16 mL) was stirred at RT overnight, then diluted with ether and filtered through a glass frit. The solids were washed with ether, and the filtrate was concentrated in vacuo, to provide the title compound as a beige solid. LRMS m/z (M+H) 207.3 found, 207.1 required.

Intermediate F: Preparation of 4-(2H-1,2,3-Triazol-2-yl)thiophene-3-carboxylic acid

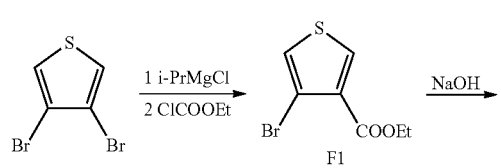

Step 1: 4-Bromo-thiophene-3-carboxylic acid ethyl ester (F1)

To a solution of 3,4-dibromothiophene (30 g, 0.12 mol) in THF (200 mL) at 0° C. was added i-PrMgCl (2.0 M solution in THF, 77 mL, 0.15 mol), keeping the temperature below 5° C. The resulting mixture was stirred at 0-5° C. for 5 h, ethyl chloroformate (14.4 mL, 0.15 mol) added dropwise at <10° C. and the resulting mixture warmed to RT, stirred overnight and quenched with the sat. aqueous $NH_4Cl$. Most of the THF was then removed in vacuo, water added and the mixture extracted with EtOAc (80 mL×4). The combined organic layers were dried over $Na_2SO_4$, filtered, the filtrate concentrated in vacuo and the crude product purified by chromatography on silica gel (petroleum ether: EtOAc=300:1) to provide the title compound as a brown oil.

Step 2: 4-Bromo-thiophene-3-carboxylic acid (F2)

To a solution of the product from step 1 (10 g, 43 mmol) in methanol (60 mL) was added sodium hydroxide (3.4 g, 86 mmol) and water (1 mL) and the mixture was stirred at RT overnight. The mixture was concentrated in vacuo, the residue diluted with water (30 mL) and extracted with EtOAc (25 mL×4). The pH of aqueous layer was adjusted to ~3 with 1M HCl and the aqueous phase extracted with EtOAc (25 mL×4). The combined extracts were dried over $Na_2SO_4$, filtered and the filtrate concentrated in vacuo to provide the title compound as a yellow solid. LRMS m/z (M+H) 206.9, 208.9 found, 206.9, 208.9 required.

Step 3: 4-(2H-1,2,3-Triazol-2-yl)thiophene-3-carboxylic acid (Intermediate F)

To a mixture of the product from step 2 (7.9 g, 38 mmol), cesium carbonate (24.8 g, 76 mmol) and CuI (2.88 g, 7.6 mmol) in DMF (200 mL) were added 2H-[1,2,3]triazole (5.24 g, 76 mmol) and N,N'-dimethyl-cyclohexane-1,2-diamine (0.9 g, 6.5 mmol) and the mixture was heated to 110° C. overnight. The cooled reaction mixture was adjusted to ~pH 12 with 1M sodium hydroxide and extracted with EtOAc (50 mL×3). The aqueous layer was adjusted to ~pH 4 with 1M HCl and extracted with EtOAc (50 mL×4). The extracts was dried over $Na_2SO_4$, filtered, the filtrate concentrated in vacuo and the residue purified by chromatography on silica (petroleum ether:EtOAc=10:1) to provide the title compound. LRMS m/z (M+H) 196.0 found, 196.0 required.

Intermediate G: Preparation of
4-fluoro-2-(2H-1,2,3-triazol-2-yl)benzoic acid

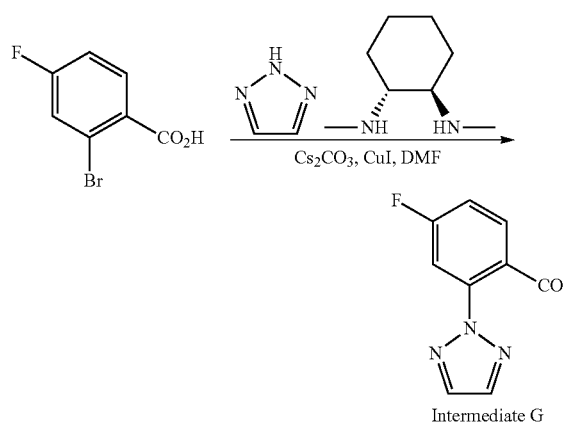

Intermediate G

To a mixture of 2-bromo-4-fluorobenzoic acid (30 g, 137 mmol), cesium carbonate (89.26 g, 274 mmol) and CuI (5.27 g, 27.4 mmol) in DMF (200 mL) were added N,N'-dimethylcyclohexane-1,2-diamine (3.7 mL, 23.3 mmol) and 1H-1,2,3-triazole (18.92 g, 274 mmol). The resulting mixture was stirred at 110° C. overnight, cooled, concentrated in vacuo and diluted with water (150 mL). The aqueous layer was extracted with EtOAc (300 mL×3). The aqueous layer was acidified with 2N HCl and extracted with EtOAc (300 mL×4). The combined organic layers were washed with brine (150 mL×3), dried over Na$_2$SO$_4$, filtered and the filtrate concentrated in vacuo. The residue was purified by chromatography on silica gel (petroleum ether:EtOAc=100: 1~5:1) to provide the title compound as a yellow solid. LRMS m/z (M+H) 208.0 found, 208.0 required.

The following Examples describe the preparation of compounds of the invention.

EXAMPLE 1

Ethyl 2-((3R,6R)-1-(2-(2H-1,2,3-triazol-2-yl)benzoyl)-6-methylpiperidin-3-yl)thiazole-5-carboxylate

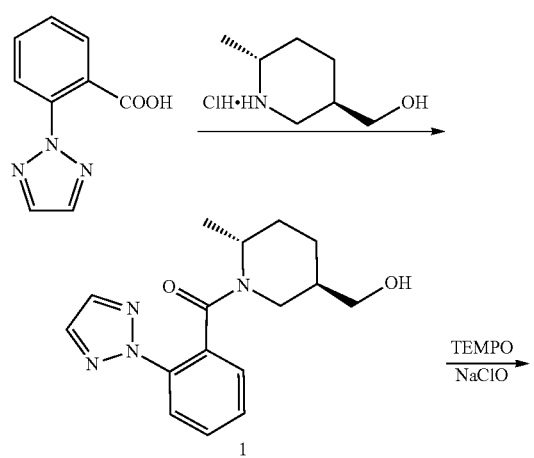

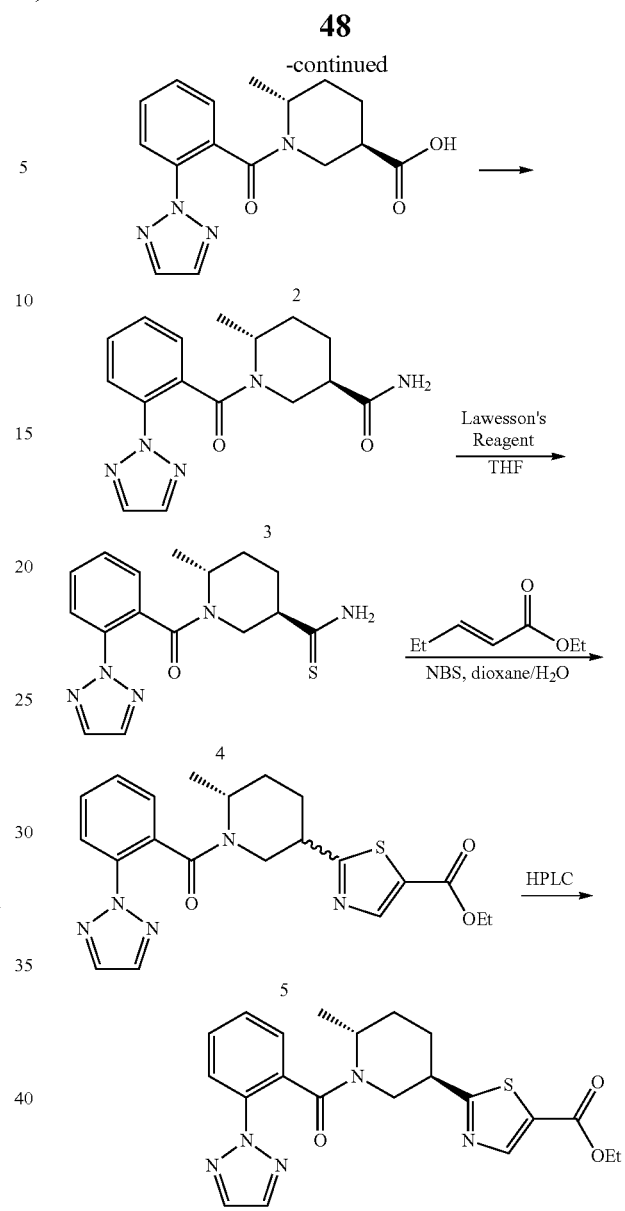

Example 1

Step 1: (2-(2H-1,2,3-Triazol-2-yl)phenyl)((2R,5R)-5-(hydroxymethyl)-2-methylpiperidin-1-yl)methanone (1)

A solution of 2-(2H-1,2,3-triazol-2-yl)benzoic acid (P. Coleman, J. Schreier, WO2007/126934) (500 mg, 2.64 mmol) in SOCl$_2$ (5 mL) was heated to reflux for 1 hour, cooled and concentrated in vacuo. The oil was dissolved in toluene (5 mL) and added to a solution of ((3R,6R)-6-methylpiperidin-3-yl)methanol hydrochloride (M. Giradin et al, Org. Proc. Res. Dev. 2013, 17, 61-68) (437 mg, 2.65 mmol) in toluene (5 mL), then aq. sodium hydroxide (5.3 mL, 1 mol/L) was added. The mixture was stirred at 10° C. for 12 h, poured into water (5 mL) and extracted with EtOAc (5 mL×3). The combined organic layers were dried over Na$_2$SO$_4$, filtered and concentrated in vacuo and the residue purified by chromatography on silica (petroleum ether: EtOAc=5:1 to petroleum ether: EtOAc=1:1) to afford the title compound. LRMS m/z (M+H) 301.2 found, 301.2 required.

Step 2: (3R,6R)-1-(2-(2H-1,2,3-Triazol-2-yl)benzoyl)-6-methylpiperidine-3-carboxylic acid (2)

To a solution of the product from step 1 (9.03 g, 30.1 mmol) in acetonitrile (80 mL) was added aqueous Na$_2$HPO$_4$ (100 mL) and TEMPO (0.47 g, 3.01 mmol). The resulting mixture was warmed to 35° C., then a solution of NaClO$_2$ (5.4 g, 60.2 mmol) in (100 mL) water and NaClO (6.1 mL, 6%) added simultaneously over 10 min and the resulting mixture stirred at 35° C. overnight. After removal of most of the acetonitrile in vacuo, the resulting mixture was extracted with DCM (3×100 mL). The organic layers were combined and washed with 200 mL of sat. sodium bisulfate solution. Product was purified by extracting into 200 mL of 1M sodium hydroxide which was washed with 2×100 mL of DCM. The aqueous phase was acidified with sat. aqueous citric acid to pH 3, extracted with DCM (3×200 mL), the combined three extracts dried over MgSO$_4$, filtered and the solvent evaporated to give the title compound used directly in the next step. LRMS m/z (M+H) 315.1 found, 315.1 required.

Step 3: (3R,6R)-1-(2-(2H-1,2,3-Triazol-2-yl)benzoyl)-6-methylpiperidine-3-carboxamide (3)

To a solution of the product from step 2 (800 mg, 2.55 mmol) in DMF (30 mL) were added HATU (1.2 g, 3.1 mmol), DIEA (0.4 g, 3.1 mmol) and ammonium chloride (273 mg, 5.1 mmol) and the mixture stirred at RT overnight. The reaction mixture was diluted with water (10 mL), extracted with DCM (10 mL×3), the combined organic layer was washed with brine (10 mL), dried over MgSO$_4$ and concentrated in vacuo. The crude product was purified by chromatography on silica (DCM:methanol=20:1) to give the title compound. LRMS m/z (M+H) 314.2 found, 314.2 required.

Step 4: (3R,6R)-1-(2-(2H-1,2,3-Triazol-2-yl)benzoyl)-6-methylpiperidine-3-carbothioamide (4)

To a solution of the product from step 3 (1.1 g, 3.5 mmol) in THF (40 mL) was added Lawesson's Reagent (781 mg, 1.93 mmol) at 27° C. The resulting mixture was stirred at the same temperature under nitrogen atmosphere for 16 h. Water (50 mL) was added and the mixture extracted with EtOAc (150 mL×3). The combined organic layers were washed with brine, dried over Na$_2$SO$_4$, filtered and concentrated in vacuo. The residue was purified by chromatography on silica (9-50% EtOAc in petroleum ether) to give the title compound as a yellow oil. LRMS m/z (M+H) 330.1 found, 330.1 required.

Step 5: Ethyl 2-((6R)-1-(2-(2H-1,2,3-triazol-2-yl)benzoyl)-6-methylpiperidin-3-yl)thiazole-5-carboxylate (5)

To a mixture of ethyl 3-ethoxyacrylate (171 mg, 1.19 mmol) in dioxane/water (12 mL/12 mL) was added NBS (224 mg, 1.27 mmol) at 0-5° C. After stirring for 1.5 h at 25° C., the product from step 4 (300 mg, 0.91 mmol) was added. The resulting mixture was heated to 110° C. for 16 h. The cooled reaction mixture was extracted with EtOAc (50 mL×3), the combined organic layers washed with brine, dried over Na$_2$SO$_4$, filtered and concentrated in vacuo. The crude product was purified by chromatography on silica (9-50% EtOAc in petroleum ether) to give the title compound (305 mg) (mixture of cis and trans isomers) as a yellow solid. LRMS m/z (M+H) 426.2 found, 426.2 required.

Step 6: Ethyl 2-((3R,6R)-1-(2-(2H-1,2,3-triazol-2-yl)benzoyl)-6-methylpiperidin-3-yl)thiazole-5-carboxylate (Example 1)

The mixture of cis and trans isomers from step 5 (50 mg, 0.12 mol) was separated by prep-HPLC to give the title compound as yellow solid. LRMS m/z (M+H) 426.2 found, 426.2 required.

EXAMPLE 2 & EXAMPLE 3

(2-(2H-1,2,3-Triazol-2-yl)phenyl)((2R,5R)-5-(5-(2-hydroxypropan-2-yl)thiazol-2-yl)-2-methylpiperidin-1-yl)methanone (Example 2)

(2-(2H-1,2,3-Triazol-2-yl)phenyl)((2R,5S)-5-(5-(2-hydroxypropan-2-yl)thiazol-2-yl)-2-methylpiperidin-1-yl)methanone (Example 3)

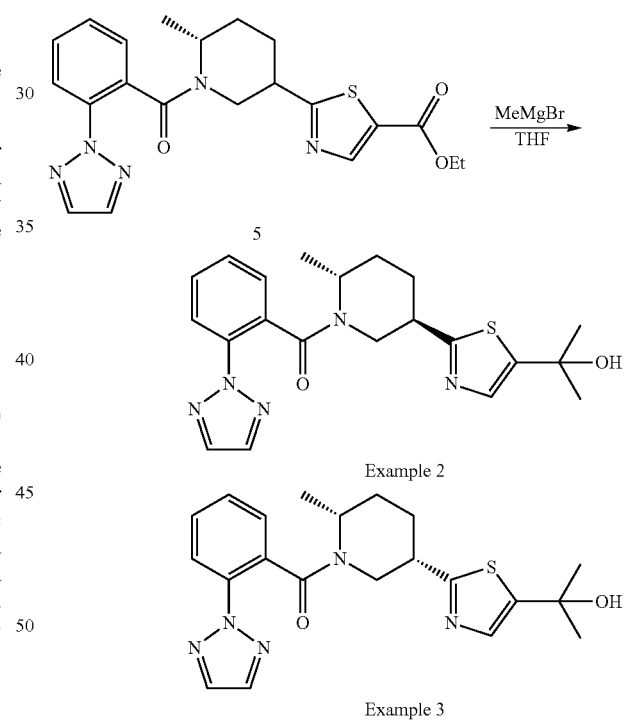

Example 2

Example 3

To a solution of ethyl 2-((6R)-1-(2-(2H-1,2,3-triazol-2-yl)benzoyl)-6-methylpiperidin-3-yl)thiazole-5-carboxylate (Example 1, compound 5) (150 mg 0.353 mmol) in THF (10 mL) was added methylmagnesium bromide (1.2 mL, 3.6 mmol, 3M in ether) at −70° C.; the mixture was allowed to warm to RT and stirred 16 h. Saturated aqueous ammonium chloride (10 mL) was added at 0~5° C. and the mixture extracted with EtOAc (15 mL×3). The combined organic layers were dried over Na$_2$SO$_4$, filtered and concentrated in vacuo. The crude products were purified by prep-HPLC to give the title compounds Example 2 and Example 3 as white solids. LRMS m/z (M+H) 412.2 found, 412.2 required.

EXAMPLE 4

(2-(2H-1,2,3-triazol-2-yl)phenyl)((2R,5R)-5-(2-(2-hydroxypropan-2-yl)thiazol-5-yl)-2-methylpiperidin-1-yl)methanone

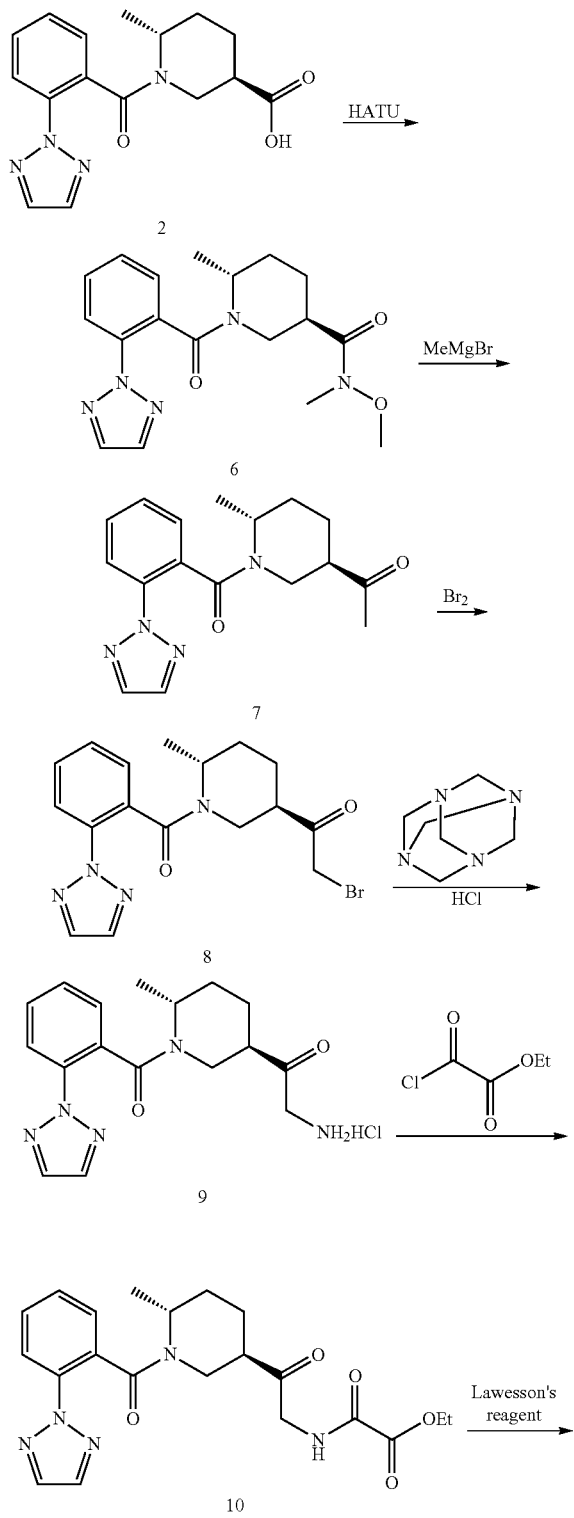

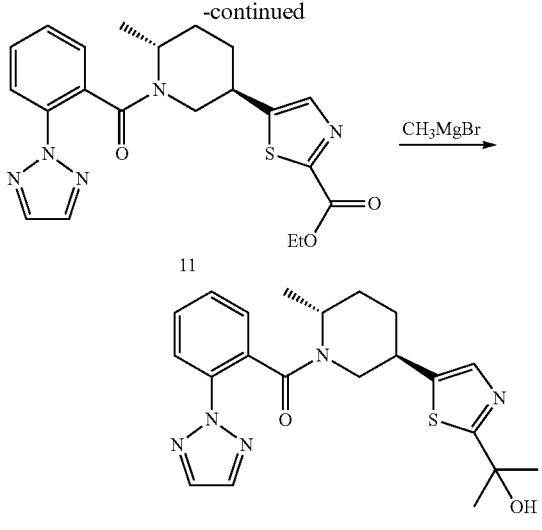

Example 4

Step 1: (3R,6R)-1-(2-(2H-1,2,3-Triazol-2-yl)benzoyl)-N-methoxy-N,6-dimethylpiperidine-3-carboxamide (6)

To a solution of compound 2 (Example 1, step 2) (1 g, 3.18 mmol) in DCM (10 mL) was added N,O-dimethylhydroxylamine hydrochloride (624 mg, 6.37 mmol), HATU (1.6 g, 4.13 mmol) and DIPEA (1.6 g, 12.72 mmol). The resulting mixture was stirred at RT for 12 h, poured into water and extracted with EtOAc (200 mL×3). The combined organic layers washed with brine, dried over MgSO₄, filtered and concentrated in vacuo. The residue was purified by chromatography on silica (9-16% EtOAc in petroleum ether) to give the title compound as a yellow oil. LRMS m/z (M+H) 358.2 found, 358.2 required.

Step 2: 1-((3R,6R)-1-(2-(2H-1,2,3-Triazol-2-yl)benzoyl)-6-methylpiperidin-3-yl)ethanone (7)

To a solution of the product from step 1 (1.0 g, 2.79 mmol) in dry THF (15 mL) at 0° C. was added a solution of methylmagnesium bromide (2.8 mL, 3M, 8.38 mmol) dropwise. The mixture was stirred at 0° C. for 1 h, water (10 mL) added and the mixture extracted with EtOAc (50 mL×3). The combined organic layers were dried over MgSO₄, filtered and concentrated in vacuo. The crude product was purified by chromatography on silica (9-33% EtOAc in petroleum ether) to give the title compound. LRMS m/z (M+H) 313.2 found, 313.2 required.

Step 3: 1-((3R,6R)-1-(2-(2H-1,2,3-Triazol-2-yl)benzoyl)-6-methylpiperidin-3-yl)-2-bromoethanone (8)

To a solution of the product from step 2 (500 mg, 1.59 mmol) in dry methanol (35 mL) was added dropwise a solution of bromine (256 mg, 1.59 mmol) in methanol (5 mL). The resulting mixture was stirred at 60° C. for 1 h, cooled to RT, poured into water and extracted with EtOAc (100 mL×3). The combined organic layers were washed with brine, dried over MgSO₄, filtered and concentrated in vacuo. The crude product was purified by chromatography on silica (ethyl 9-50% acetate in petroleum ether) to give the title compound as a yellow oil. LRMS m/z (M+H) 391.1, 393.1 found, 391.1, 393.1 required.

Step 4: 1-((3R,6R)-1-(2-(2H-1,2,3-Triazol-2-yl)benzoyl)-6-methylpiperidin-3-yl)-2-aminoethanone hydrochloride (9)

To a solution of the product from step 3 (50 mg, 0.13 mmol) in DCM (1.2 mL) was added hexamethylenetramine (18 mg, 0.13 mmol). The mixture was stirred at RT for 12 h, filtered and the residue was dissolved in ethanolic HCl (0.2 mL HCl in 0.6 mL of ethanol). The mixture was stirred at RT for 1 h and concentrated in vacuo to give the crude product, which was used directly in the next step without further purification. LRMS m/z (M+H) 328.2 found, 328.2 required.

Step 5: Ethyl 2-((2-((3R,6R)-1-(2-(2H-1,2,3-triazol-2-yl)benzoyl)-6-methylpiperidin-3-yl)-2-oxoethyl)amino)-2-oxoacetate (10)

To a solution of the product from step 4 (360 mg, 0.99 mmol) and triethylamine (400 mg, 3.96 mmol) in dry DCM (4 mL) at 0° C. was added dropwise a solution of ethyl 2-chloro-2-oxoacetate (162 mg, 1.18 mmol). The resulting mixture was stirred at 0° C. for 1 h, water (10 mL) added and the mixture extracted with EtOAc (50 mL×3). The combined organic layers were dried over MgSO₄, filtered and concentrated in vacuo. The crude product was purified by prep-HPLC to give the title compound. LRMS m/z (M+H) 428.0 found, 428.2 required.

Step 6: ethyl 5-((3R,6R)-1-(2-(2H-1,2,3-Triazol-2-yl)benzoyl)-6-methylpiperidin-3-yl)thiazole-2-carboxylate (11)

A solution of the product from step 5 (150 mg, 0.35 mmol) and Lawesson's reagent (170 mg, 0.42 mmol) in dry THF (3 mL) was stirred at 60° C. for 6 h. After cooling to RT, the mixture was concentrated in vacuo. The residue was purified by Prep-TLC (66% EtOAc in petroleum ether) to give the title compound. LRMS m/z (M+H) 426.0 found, 426.2 required.

Step 7: (2-(2H-1,2,3-Triazol-2-yl)phenyl)((2R,5R)-5-(2-(2-hydroxypropan-2-yl)thiazol-5-yl)-2-methylpiperidin-1-yl)methanone (Example 4)

To a solution of methylmagnesium bromide (0.1 mL, 0.12 mmol) in dry THF (0.5 mL) at −78° C. under nitrogen atmosphere was added dropwise a solution of the product from step 6 (50 mg, 0.12 mmol) in THF (3 mL). The resulting mixture was stirred at −78° C. for 30 min, saturated aqueous ammonium chloride added and the mixture extracted with EtOAc (50 mL×3). The combined organic layers were washed with brine, dried over MgSO₄, filtered, and concentrated in vacuo. The residue was purified by Prep-HPLC to give the title compound as white solid. LRMS m/z (M+H) 412.1 found, 412.2 required.

EXAMPLE 5

((2-(2H-1,2,3-Triazol-2-yl)phenyl)((2R,5R)-5-(4-(2-hydroxypropan-2-yl)thiazol-2-yl)-2-methylpiperidin-1-yl)methanone

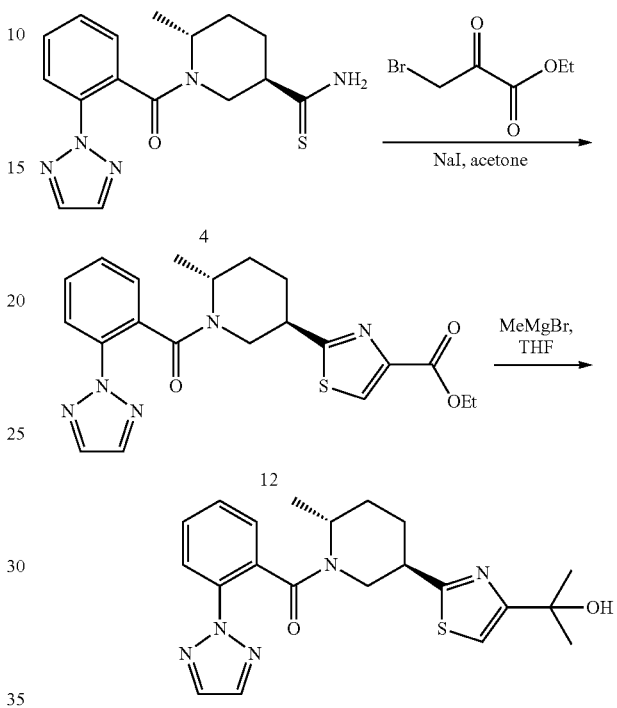

Example 5

Step 1: (2-(2H-1,2,3-triazol-2-yl)phenyl)((2R,5R)-2-methyl-5-(4-phenyloxazol-2-yl)piperidin-1-yl)methanone (12)

To a solution of compound 4 (example 1 step 4) (200 mg, 0.61 mmol) and ethyl 3-bromo-2-oxopropanoate (119 mg, 0.61 mmol) in THF (10 mL) was added NaI (91 mg, 0.61 mmol). The resulting mixture was stirred at 50° C. for 2 hours, cooled to RT and concentrated in vacuo. The crude product was purified by Prep-TLC (66% EtOAc in petroleum ether) to give the title compound. LRMS m/z (M+H) 426.2 found, 426.2 required.

Step 2: (2-(2H-1,2,3-triazol-2-yl)phenyl) ((2R,5R)-5-(4-(2-hydroxypropan-2-yl)thiazol-2-yl)-2-methylpiperidin-1-yl)methanone (Example 5)

To a solution of methylmagnesium bromide (0.12 mL, 0.38 mmol) in dry THF (10 mL) at 0° C. under nitrogen atmosphere was added the product from step 1 (80 mg, 0.19 mmol) dropwise. The resulting mixture was stirred at RT overnight, quenched with sat. ammonium chloride solution and extracted with EtOAc (10 mL×3). The organic layers were combined dried over Na₂SO₄, filtered and concentrated in vacuo. The residue was purified by Prep-HPLC to give the title compound. LRMS m/z (M+H) 412.2 found, 412.2 required.

EXAMPLE 6 & EXAMPLE 7

((2-(2H-1,2,3-triazol-2-yl)phenyl)((2R,5R)-2-methyl-5-(4-((S)-2,2,2-trifluoro-1-hydroxyethyl)thiazol-2-yl)piperidin-1-yl)methanone (Example 6)

((2-(2H-1,2,3-triazol-2-yl)phenyl)((2R,5R)-2-methyl-5-(4-((S)-2,2,2-trifluoro-1-hydroxyethyl)thiazol-2-yl)piperidin-1-yl)methanone (Example 7)

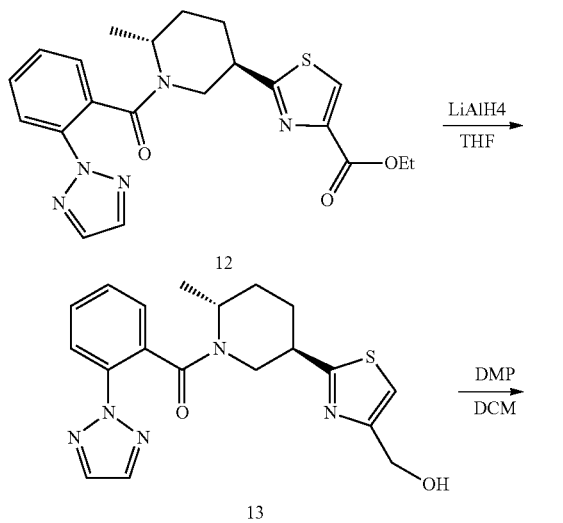

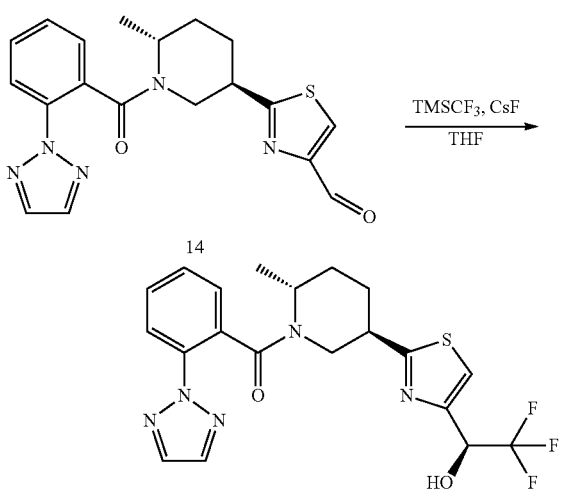

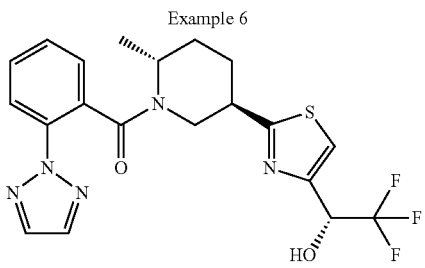

Example 6

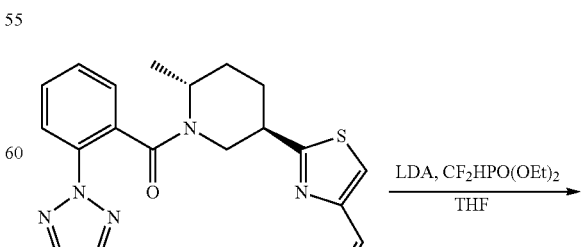

Example 7

Step 1: (2-(2H-1,2,3-Triazol-2-yl)phenyl)((2R,5R)-5-(4-(hydroxymethyl)thiazol-2-yl)-2-methylpiperidin-1-yl)methanone (13)

To a solution of compound 12 (Example 5, Step 1) (305 mg, 0.717 mmol) in THF (50 mL) at 0° C. was added LAH (55 mg, 1.45 mmol) and the mixture stirred at RT for 2 h. To the re-cooled (0° C.) mixture, water (1 mL) was added and resulting mixture dried over $Na_2SO_4$. The mixture was filtered and concentrated in vacuo to give the title compound as a pale yellow solid, which was used in the next step directly. LRMS m/z (M+H) 384.1 found, 384.1 required.

Step 2: 2-((3R,6R)-1-(2-(2H-1,2,3-triazol-2-yl)benzoyl)-6-methylpiperidin-3-yl)thiazole-4-carbaldehyde (14)

A mixture of the product from step 1 (280 mg, 0.73 mmol) and Dess Martin periodinane (62 mg, 1.46 mmol) in DCM (30 mL) was stirred at RT overnight. The mixture was concentrated in vacua and purified by chromatography on silica (33% EtOAc in petroleum ether) to give the title compound as yellow solid. LRMS m/z (M+H) 382.1 found, 382.1 required.

Step 3: (2-(2H-1,2,3-triazol-2-yl)phenyl)((2R,5R)-2-methyl-5-(4-((S)-2,2,2-trifluoro-1-hydroxyethyl)thiazol-2-yl)piperidin-1-yl)methanone (Example 6) & (2-(2H-1,2,3-triazol-2-yl)phenyl)((2R,5R)-2-methyl-5-(4-((R)-2,2,2-trifluoro-1-hydroxyethyl)thiazol-2-yl)piperidin-1-yl)methanone (Example 7)

To a mixture of the product from step 2 (105 mg, 0.275 mmol) and CsF (84 mg, 0.553 mmol) in THF (15 mL), at 0° C. under nitrogen, was added trimethyl(trifluromethyl)silane (60 mg, 0.42 mmol) and the mixture stirred at RT for 2 h, quenched with saturated aq. ammonium chloride and extracted with EtOAc. The combined organic layers were dried over $Na_2SO_4$, filtered and concentrated in vacua. The crude product was purified by Prep-HPLC and then diastereomers separated by SFC to give the title compounds Example 6 and Example 7, respectively, as white solids. LRMS m/z (M+H) 452.1 found, 452.1 required.

EXAMPLE 8 & EXAMPLE 9

((2-(2H-1,2,3-Triazol-2-yl)phenyl)((2R,5R)-5-(4-((R)-2,2-difluoro-1-hydroxyethyl)thiazol-2-yl)-2-methylpiperidin-1-yl)methanone (Example 8)

((2-(2H-1,2,3-triazol-2-yl)phenyl)((2R,5R)-5-(4-((S)-2,2-difluoro-1-hydroxyethyl)thiazol-2-yl)-2-methylpiperidin-1-yl)methanone (Example 9)

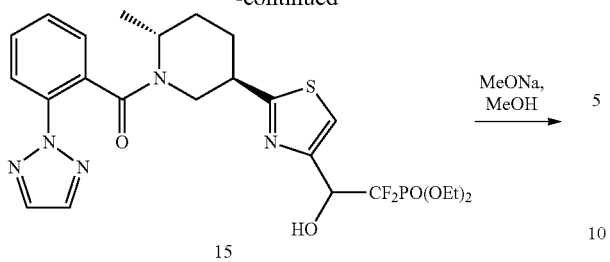

Step 1: Diethyl (2-(2-((3R,6R)-1-(2-(2H-1,2,3-triazol-2-yl)benzoyl)-6-methylpiperidin-3-yl)thiazol-4-yl)-1,1-difluoro-2-hydroxyethyl)phosphonate (15)

To a solution of compound 14 (Example 6, step 1) (80 mg, 0.21 mmol) in dry THF (2 mL), at −78° C. under nitrogen, was added dropwise LDA (0.42 mL, 2M, 0.84 mmol). The resulting mixture was stirred at −78° C. for 1 h, then a solution of ethoxy((ethylperoxy)difluoromethyl)-phosphine (80 mg, 0.21 mmol) in dry THF (1 mL) added. The resulting mixture was stirred at −78° C. for 2 h, quenched with sat. aqueous ammonium chloride solution and extracted with EtOAc (10 mL×3). The combined organic layers were dried over Na$_2$SO$_4$, filtered and concentrated in vacuo to give the title compound as a white solid, used in the next step without further purification. LRMS m/z (M+H) 570.2 found, 570.2 required.

Step 2: (2-(2H-1,2,3-triazol-2-yl)phenyl)((2R,5R)-5-(4-((R)-2,2-difluoro-1-hydroxyethyl)thiazol-2-yl)-2-methylpiperidin-1-yl)methanone (Example 8) & (2-(2H-1,2,3-triazol-2-yl)phenyl)((2R,5R)-5-(4-((S)-2,2-difluoro-1-hydroxyethypthiazol-2-yl)-2-methyl-piperidin-1-yl)methanone (Example 9)

Sodium (8 mg, 0.36 mmol) was added to dry MeOH (5 mL) and after formation of a solution, the product from step 1 (100 mg) was added and the mixture stirred at 50° C. for 4 h. After cooling to RT, the mixture was adjusted to pH 7 with 1 N HCl solution and concentrated in vacuo. The crude product was purified by Prep-HPLC and then diastereomers separated by SFC to give the title compounds Example 8 and Example 9, respectively. LRMS m/z (M+H) 434.1 found, 434.1 required.

EXAMPLE 10

((2-(2H-1,2,3-Triazol-2-yl)thiophen-3-yl)((2R,5R)-5-(4-(2-hydroxypropan-2-yl)thiazol-2-yl)-2-methyl-piperidin-1-yl)methanone

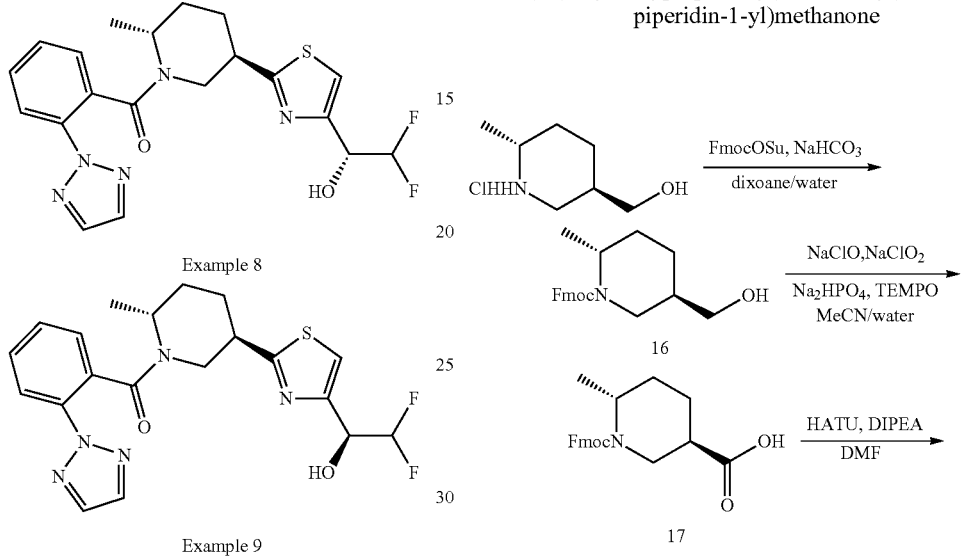

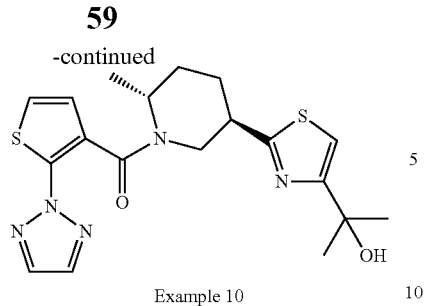

Example 10

Step 1: (2R,5R)-(9H-fluoren-9-yl)methyl 5-(hydroxymethyl)-2-methylpiperidine-1-carboxylate (16)

To a mixture of ((3R,6R)-6-methylpiperidin-3-yl)methanol hydrochloride (M. Giradin et al, *Org. Proc. Res. Dev.* 2013, 17, 61-68) (2.00 g, 12.0 mmol) in dioxane (20 mL) was added sodium bicarbonate (2.52 g, 30.0 mmol) in 5 mL of water at 0° C. $E_{moc}OSu$ (4.48 g, 13.3 mmol) in 10 mL of dioxane was added slowly and the reaction mixture stirred at RT overnight. Water (20 mL) was added and the mixture extracted with EtOAc (100 mL×3). The combined organic layers were washed with brine (20 mL×3), dried over MgSO$_4$, filtered and concentrated in vacuo. The crude product was purified by chromatography on silica (33% EtOAc in petroleum ether) to give the title compound. LRMS m/z (M+H) 352.1 found, 352.2 required.

Step 2: (3R,6R)-1-(((9H-Fluoren-9-yl)methoxy)carbonyl)-6-methylpiperidine-3-carboxylic acid (17)

To a solution of the product from step 1 (3.00 g, 8.55 mol) in acetonitrile (40 mL) was added a solution of Na$_2$HPO$_4$ (840 mg, 5.91 mmol) in 24 mL of water, and TEMPO (133 mg, 0.855 mol). The mixture was heated to 35° C. and then a solution of NaClO$_2$ (1.54 g, 17.1 mmoL) in water (10 mL) and NaClO (1.9 mL) added simultaneously. The resulting mixture was stirred at 35° C. overnight, cooled to RT and concentrated in vacuo to remove acetonitrile. Water (50 mL) was added and the mixture was adjusted to pH 5 with 2 M HCl, and extracted with EtOAc (100 mL×3). The combined organic layers were washed with brine (20 mL×3), dried over MgSO$_4$, filtered and concentrated in vacuo to give the title compound, which was used in the next step directly. LRMS m/z (M+H) 366.1 found, 366.2 required.

Step 3: (2R,5R)-(9H-Fluoren-9-yl)methyl 5-carbamoyl-2-methylpiperidine-1-carboxylate (18)

To a solution of the product from step 2 (3.00 g, 8.20 mmol) in DCM (30 mL) was added HATU (4.20 g, 11.0 mmol), triethylamine (3.00 mL, 20.0 mmol) and ammonium chloride (660 mg, 12.3 mmol) and the mixture stirred at RT overnight. The reaction mixture was diluted with water (30 mL), and extracted with DCM (50 mL×3), the combined organic layers washed with brine (20 mL×3), dried over Na$_2$SO$_4$, filtered and concentrated in vacua. The crude product was purified by chromatography on silica (50% EtOAc in petroleum ether) to give the title compound. LRMS m/z (M+H) 365.1 found, 365.2 required.

Step 4: (2R,5R)-(9H-Fluoren-9-yl)methyl 5-carbamothioyl-2-methylpiperidine-1-carboxylate (19)

To a solution of the product from step 3 (5.6 g, 15.37 mmol) in THF was added Lawesson's reagent (6.2 g, 15.33 mmol). The resulting mixture was stirred at RT overnight, concentrated in vacua and the crude product purified by chromatography on silica (33% EtOAc in petroleum ether) to give the title compound as yellow oil. LRMS m/z (M+H) 381.2 found, 381.2 required.

Step 5: Ethyl 2-((3R,6R)-1-(((9H-fluoren-9-yl)methoxy)carbonyl)-6-methylpiperidin-3-yl)thiazole-4-carboxylate (20)

To a solution of the product from step 4 (4.5 g, 11.83 mmol) in THF (100 mL) was added ethyl 2-bromo-2-oxoacetate (6.1 g, 23.46 mmol) and the mixture heated to 60° C. for 45 min. The cooled reaction mixture was concentrated in vacua and purified by chromatography on silica (33% EtOAc in petroleum ether) to give the title compound as white solid. LRMS m/z (M+H) 477.2 found, 477.2 required.

Step 6: (2S,5S)-(9H-Fluoren-9-yl)methyl 5-(4-(2-hydroxypropan-2-yl)thiazol-2-yl)-2-methylpiperidine-1-carboxylate (21)

To a solution of the product from step 5 (1.05 g, 2.20 mmol) in THF at 0° C. under nitrogen was added methylmagnesium bromide (3.7 mL, 12.3 mmol) and the resulting mixture stirred at RT for 3 h. TLC (33% EtOAc in petroleum ether) showed the reaction was completed. The reaction mixture was quenched with ammonium chloride (30 mL), and extracted with EtOAc (100 mL×3). The combined organic layers were washed with brine (10 mL), dried over Na$_2$SO$_4$, filtered and concentrated in vacuo and the crude product purified by chromatography on silica (33% EtOAc in petroleum ether) to give the title compound as white solid. LRMS m/z (M+H) 463.2 found, 463.2 required.

Step 7: 2-(2-((3R,6R)-6-methylpiperidin-3-yl)thiazol-4-yl)propan-2-ol (22)

To a solution of the product from step 6 (700 mg, 0.65 mmol) in methanol (15 mL) was added piperidine (3 mL) at 0° C. and the resulting mixture stirred at RT overnight, concentrated in vacuo and the purified by silica gel gradient chromatography (16.7% methanol in DCM) to give the title compound as yellow oil. LRMS m/z (M+H) 241.1 found, 241.1 required.

Step 8: (2-(2H-1,2,3-triazol-2-yl)thiophen-3-yl)((2R,5R)-5-(4-(2-hydroxypropan-2-yl)thiazol-2-yl)-2-methylpiperidin-1-yl)methanone (Example 10)

A solution of the product from step 7 (300 mg, 1.25 mmol), 2-(2H-1,2,3-triazol-2-yl)thiophene-3-carboxylic acid (Intermediate D) (292 mg, 1.50 mmol), DIPEA (320 mg, 2.48 mmol) and HATU (712 mg, 1.87 mmol) in DMF (50 mL) was at stirred at RT overnight. The mixture was diluted with water (100 mL), extracted with EtOAc (100 mL×3), the combined organic layers washed with brine, dried over Na$_2$SO$_4$, filtered and concentrated in vacuo. The crude product was purified by chromatography on silica (50% EtOAc in petroleum ether) to give the title compound as a white solid. LRMS m/z (M+H) 418.1 found, 418.1 required.

The following compounds were prepared according to the general procedure of step 8 provided in Example 10, substituting the appropriate acid with (2S,5S)-(9H-fluoren-9-yl)methyl 5-(4-(2-hydroxypropan-2-yl)thiazol-2-yl)-2-methylpiperidine-1-carboxylate. The starting materials are either commercially available or may be prepared as described in the synthesis of intermediates A-G.

TABLE 1

The following compounds werre prepared according to the general procedure of step 8 provided in Example 10, substituting the appropriate acid with (2S,5S)-(9H-fluoren-9-yl)methyl 5-(4-(2-hydroxypropan-2-yl)thiazol-2-yl)-2-methylpiperidine-1carboxylate. The starting materials are either commercially available or may be prepared as described in the synthesis of intermediates A-G.

| Example | R | IUPAC Name | LRMS or HRMS (M + H⁺) |
|---|---|---|---|
| 11 | | 1-(2-((2R,5R)-5-(4-(2-Hydroxypropan-2-yl)thiazol-2-yl)-2-methylpiperidine-1-carbonyl)phenyl)cyclopropanecarbonitrile | Calc'd 410.1, found 410.1 |
| 12 | | Methyl 2-((2R,5R)-5-(4-(2-hydroxypropan-2-yl)thiazol-2-yl)-2-methylpiperidine-1-carbonyl)benzoate | Calc'd 403.1, found 403.1 |

EXAMPLE 13

(4-fluoro-2-(2H-1,2,3-triazol-2-yl)phenyl)((2R,5R)-5-(4-(2-hydroxypropan-2-yl)thiazol-2-yl)-2-methyl-piperidin-1-yl)methanone

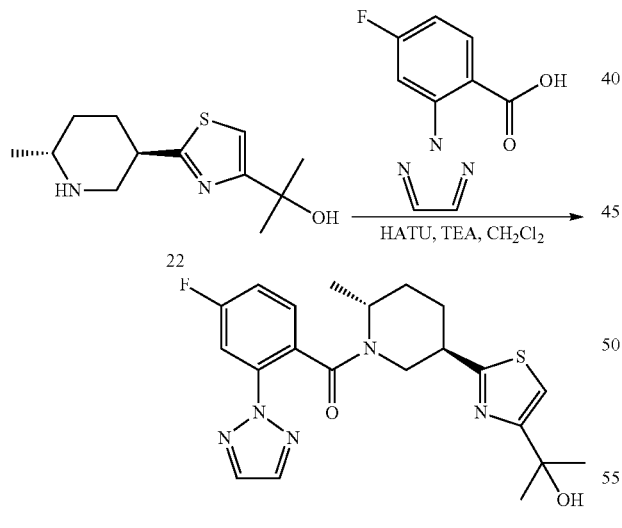

Example 13

Step 1: (4-Fluoro-2-(2H-1,2,3-triazol-2-yl)phenyl) ((2R,5R)-5-(4-(2-hydroxypropan-2-yl)thiazol-2-yl)-2-methylpiperidin-1-yl)methanone (Example 13)

To a mixture of piperidine intermediate 22 (Example 10, Step 7) (250 mg, 1.04 mmol), 4-fluoro-2-(2H-1,2,3-triazol-2-yl)benzoic acid (Intermediate G) (238 mg, 1.15 mmol) and HATU (475 mg, 1.25 mmol) in DCM (15 mL) was added triethylamine (158 mg, 1.56 mmol) at RT. The resulting mixture was stirred at RT overnight, concentrated in vacua and the residue purified by prep-HPLC to give the title compound as a white solid. LRMS m/z (M+H) 430.1 found, 430.1 required.

EXAMPLE 14

(2-(2H-Tetrazol-2-yl)phenyl)((2R,5R)-5-(4-(2-hydroxypropan-2-yl)thiazol-2-yl)-2-methylpiperidin-1-yl)methanone

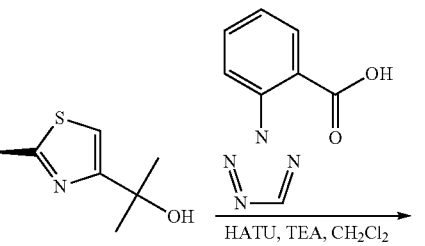

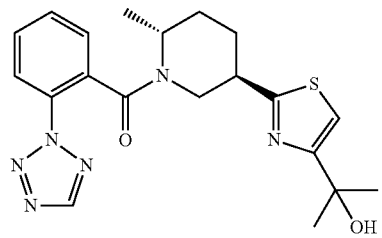

Example 14

Step 1: (2-(2H-Tetrazol-2-yl)phenyl)((2R,5R)-5-(4-(2-hydroxypropan-2-yl)thiazol-2-yl)-2-methylpiperidin-1-yl)methanone (Example 14)

To a mixture of piperidine intermediate 22 (Example 10, Step 7) (250 mg, 1.04 mmol), 2-(2H-tetrazol-2-yl)benzoic acid (Intermediate C) (220 mg, 1.16 mmol) and HATU (475 mg, 1.25 mmol) in DCM (15 mL) was added triethylamine (158 mg, 1.56 mmol) at RT. The resulting mixture was stirred at RT overnight, concentrated in vacuo and the residue purified by prep-HPLC to give the title compound as a white solid. LRMS m/z (M+H) 413.1 found, 413.1 required.

EXAMPLE 15

(4-(2H-1,2,3-Triazol-2-yl)thiophen-3-yl)((2R,5R)-5-(4-(2-hydroxypropan-2-yl)thiazol-2-yl)-2-methylpiperidin-1-yl)methanone

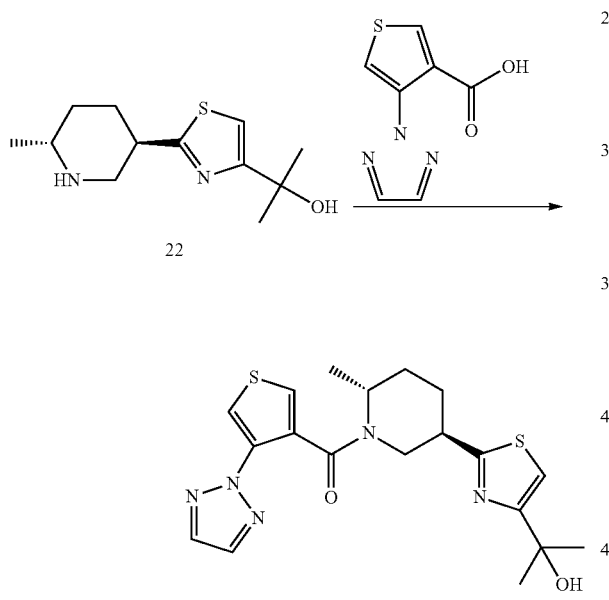

Example 15

Step 1: (4-(2H-1,2,3-triazol-2-yl)thiophen-3-yl)((2R,5R)-5-(4-(2-hydroxypropan-2-yl)thiazol-2-yl)-2-methylpiperidin-1-yl)methanone (Example 15)

A solution of 4-(2H-1,2,3-triazol-2-yl)thiophene-3-carboxylic acid (Intermediate F) (146 mg, 0.749 mmol) and SOCl$_2$ (5 mL) was heated to reflux for 1 h, cooled to RT and concentrated in vacuo. The residue was dissolved in DCM (5 mL) and added to a solution of piperidine intermediate 22 (Example 10, Step 7) (150 mg, 0.624 mmol) and triethylamine (190 mg, 1.88 mmol) in DCM (20 mL) at 0° C. The resulting mixture was stirred at RT overnight, concentrated in vacuo and the residue purified by prep-HPLC to give the title compound as a white solid. LRMS m/z (M+H) 418.1 found, 418.1 required.

EXAMPLE 16

((2R,5R)-5-(4-(2-hydroxypropan-2-yl)thiazol-2-yl)-2-methylpiperidin-1-yl)(4-(pyrimidin-2-yl)thiophen-3-yl)methanone

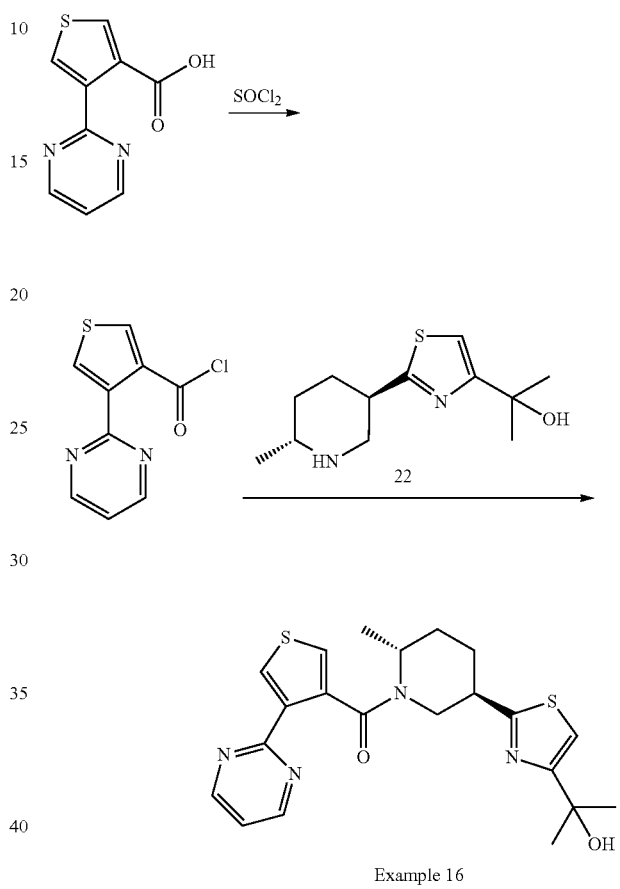

Example 16

Step 1: (4-(2H-1,2,3-triazol-2-yl)thiophen-3-yl)((2R,5R)-5-(4-(2-hydroxypropan-2-yl)thiazol-2-yl)-2-methylpiperidin-1-yl)methanone (Example 16)

To a solution of 4-(pyrimidin-2-yl)thiophene-3-carboxylic acid (Intermediate B) (50 mg, 0.25 mmol) in dry DCM (5 mL) at 0° C. under nitrogen was added thionyl chloride (0.5 mL) dropwise. The resulting mixture was heated to reflux with stirring for 2 h, cooled to RT and concentrated in vacuo. The residue was dissolved in DCM (5 mL) and added dropwise to a solution of 2-(2-((3R,6R)-6-methylpiperidin-3-yl)thiazol-4-yl)propan-2-ol (Example 10, step 7) (30 mg, 0.12 mmol) and DIPEA (148 mg, 1.15 mmol) in DCM (15 mL). The resulting mixture was stirred at RT overnight, concentrated in vacuo and purified by Prep-HPLC to give the title compound as a white solid. LRMS m/z (M+H) 429.1 found, 429.1 required.

EXAMPLE 17

((2R,5R)-5-(4-(2-Hydroxypropan-2-yl)thiazol-2-yl)-2-methylpiperidin-1-yl)(2-(pyrimidin-2-yl)phenyl)methanone

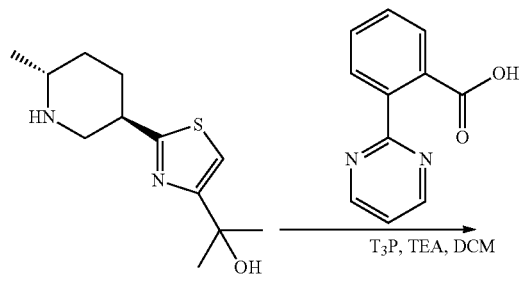

Step 1: ((2R,5R)-5-(4-(2-hydroxypropan-2-yl)thiazol-2-yl)-2-methylpiperidin-1-yl)(2-(pyrimidin-2-yl)phenyl)methanone (Example 17)

To a solution of piperidine intermediate 22 (Example 10, Step 7) (30 mg, 0.12 mmol), 2-(pyrimidin-2-yl)benzoic acid (50 mg, 0.25 mmol) and DIPEA (32 mg, 0.25 mmol) in DCM (5 mL) was added T$_3$P (0.5 mL) at 0° C. The resulting mixture was stirred at 50° C. overnight, cooled to RT, concentrated in vacua and the residue purified by Prep-HPLC to give the title compound as white solid. LRMS m/z (M+H) 423.1 found, 423.1 required.

The following compound was prepared according to the general procedure provided in Example 17, substituting 2-(pyrimidin-2-yl)benzoic acid with 2-(pyrimidin-2-yl)thiophene-3-carboxylic acid (Intermediate E).

TABLE 2

The following compound was prepared according to the general procedure provided in Example 17, substituting 2-(pyrimidin-2-yl)benzoic acid with 2-(pyrimidin-2-yl)thiophene-3-carboxylic acid (Intermediate E).

| Example | R | IUPAC Name | LRMS or HRMS (M + H⁺) |
|---|---|---|---|
| 18 | 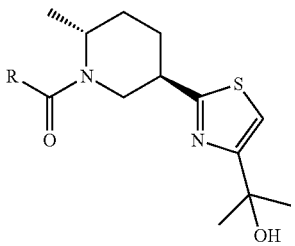 | ((2R,5R)-5-(4-(2-Hydroxypropan-2-yl)thiazol-2-yl)-2-methylpiperidin-1-yl)(2-(pyrimidin-2-yl)thiophen-3-yl)methanone | Calc'd 429.1, found 429.1 |

-continued

Example 17

EXAMPLE 19

(2-(2H-1,2,3-Triazol-2-yl)phenyl)((2R,5R)-5-(4-(2-hydroxypropan-2-yl)-5-methylthiazol-2-yl)-2-methylpiperidin-1-yl)methanone

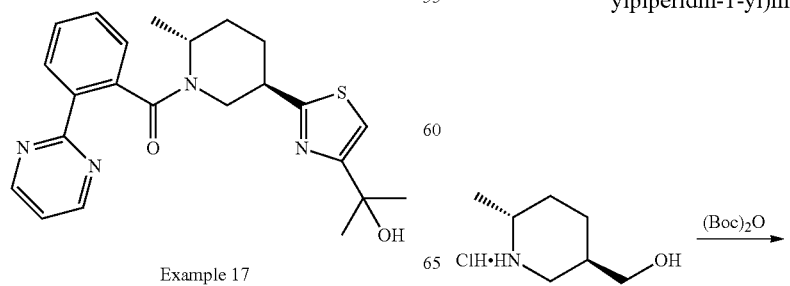

-continued

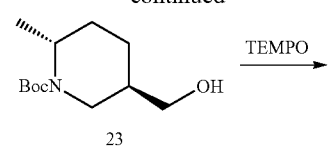
23

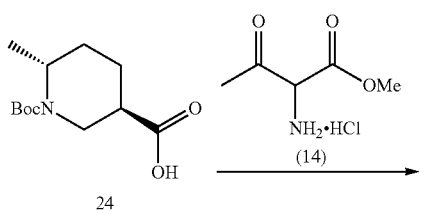
24

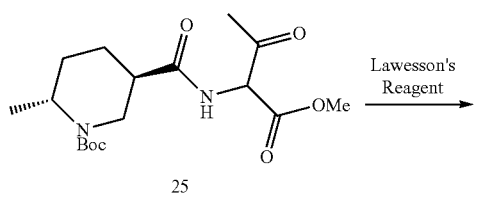
25

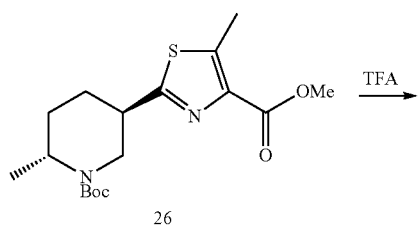
26

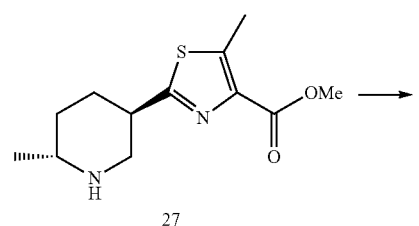
27

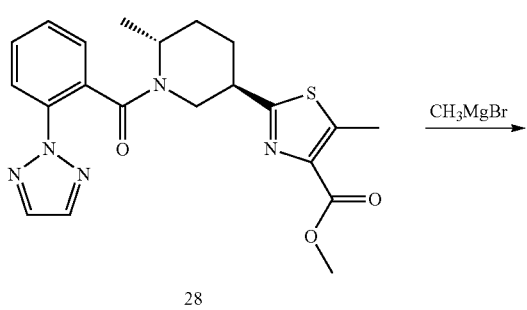
28

-continued

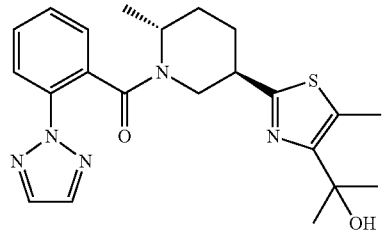

Example 19

Step 1: (2R,5R)-tert-Butyl 5-(hydroxymethyl)-2-methylpiperidine-1-carboxylate (23)

To a solution of ((3R,6R)-6-methylpiperidin-3-yl)methanol hydrochloride (M. Giradin et al, *Org. Proc. Res. Dev.* 2013, 17, 61-68) (10 g, 60.61 mmol) in THF (100 mL) and water (100 mL) was added sodium hydroxide (7.3 g, 181.82 mmol) at 0° C. After stirring for 30 min, (Boc)₂O (15.8 g, 72.73 mmol) was added and the resulting mixture stirred at RT for 9 h, diluted with water and extracted with EtOAc (300 mL×3). The combined organic layers were washed with brine, dried over MgSO₄, filtered, and concentrated in vacuo. The crude product was purified by chromatography on silica (9% EtOAc in petroleum ether) to give the title compound as a colorless oil. LRMS m/z (M+H) 230.1 found, 230.1 required.

Step 2: (3R,6R)-1-(tert-Butoxycarbonyl)-6-methyl-piperidine-3-carboxylic acid (24)

To a solution of the product from step 1 (10.5 g, 45.85 mmol) in acetonitrile (120 mL) was added a solution of Na₂HPO₄ (28.37 g, 79.25 mmol) in water, and TEMPO (715 mg, 4.6 mmol) was added. The mixture was heated to 35° C. and a solution of NaClO₂ (8.2 g, 91.7 mmoL) in water (35 mL) and NaClO (9.4 mL) added simultaneously and the mixture stirred at 35° C. overnight. The organic solvent was removed in vacuo, water (200 mL) added and the mixture adjusted pH to 5 with 1 M HCl and extracted with EtOAc (300 mL×3). The combined organic layers were washed with brine (200 mL×3), dried over MgSO₄, filtered and concentrated in vacuo to give the title compound as a white solid. LRMS m/z (M+H) 244.2 found, 244.2 required.

Step 3: (2R,5R)-tert-Butyl 5-((1-methoxy-1,3-dioxobutan-2-yl)carbamoyl)-2-methylpiperidine-1-carboxylate (25)

A mixture of the product from step 2 (3.20 g, 13.2 mmol) and thionyl chloride (10 mL) was stirred at 80° C. for 1 h, cooled to RT and concentrated in vacuo. The residue was dissolved in DCM (20 mL) and then added dropwise to a solution of methyl 2-amino-3-oxobutanoate hydrochloride (3.31 g, 19.8 mmol) in DCM (40 mL) and DIPEA (8.51 g, 66 mmol), at 0° C. The resulting mixture was stirred at RT for 12 h, poured into water and extracted with DCM (80 mL×3). The combined organic layers were washed with brine, dried over MgSO₄, filtered and concentrated in vacuo. The crude product was purified by chromatography on silica (10%~33% EtOAc in petroleum ether) to give the title compound as yellow oil. LRMS m/z (M+H) 432.1 found, 432.1 required.

Step 4: Methyl 2-((3R,6R)-1-(tert-butoxycarbonyl)-6-methylpiperidin-3-yl)-5-methylthiazole-4-carboxylate (26)

A solution of the product from step 3 (200 mg, 0.56 mmol) and Lawesson's reagents (452 mg, 1.12 mmol) in dry THF (3 mL) was stirred at 60° C. for 2 h, cooled to RT and concentrated in vacuo. The crude product was purified by Prep-TLC (33% EtOAc in petroleum ether) to give the title compound as a yellow oil. LRMS m/z (M+H) 355.2 found, 355.2 required.

Step 5: Methyl 5-methyl-2-((3R,6R)-6-methylpiperidin-3-yl)thiazole-4-carboxylate (27)

A solution of the product from step 4 (200 mg, 0.56 mmol) in trifluoroacetic acid/DCM (2 mL/2 mL) was stirred at RT for 1 h, then concentrated in vacuo to give the title compound as the TFA salt. LRMS m/z (M+H) 255.1 found, 255.1 required.

Step 6: Methyl 2-((3R,6R)-1-(2-(2H-1,2,3-triazol-2-yl)benzoyl)-6-methylpiperidin-3-yl)-5-methylthiazole-4-carboxylate (28)

A mixture of 2-(2H-1,2,3-triazol-2-yl)benzoic acid (50 mg, 0.26 mmol) in thionyl chloride (2 mL) was stirred at 80° C. for 1 h, cooled to RT and concentrated in vacuo. The residue was dissolved in DCM (10 mL) and added to a solution of the product from step 5 (66 mg, 0.26 mmol) in DCM (1 mL) and DIPEA (0.1 ml) at 0° C. The resulting mixture was stirred at RT for 12 h, poured into water and extracted with EtOAc (50 mL×3). The combined organic layers were washed with brine, dried over MgSO₄, filtered and concentrated in vacuo. The crude product was purified by Prep-TLC (50% EtOAc in petroleum ether) to give the title compound as a white solid. LRMS m/z (M+H) 426.1 found, 426.1 required.

Step 7: methyl 2-((3R,6R)-1-(2-(2H-1,2,3-triazol-2-yl)benzoyl)-6-methylpiperidin-3-yl)-5-methylthiazole-4-carboxylate (Example 19)

To a solution of the product from step 6 (50 mg, 0.12 mmol) in dry THF (2 mL) at 0° C. under nitrogen atmosphere was added dropwise methylmagnesium bromide (0.2 mL, 0.39 mmol) and the resulting mixture stirred at 0° C. for 1 h. Saturated aqueous ammonium chloride was added and the mixture extracted with EtOAc (50 mL×3). The combined organic layers were washed with brine, dried over MgSO₄, filtered, and concentrated in vacuo. The crude product was purified by Prep-HPLC to give the title compound as a white solid. LRMS m/z (M+H) 426.1 found, 426.1 required.

The following compounds were prepared according to the general procedure of step 6 and 7 provided in Example 19. The starting materials are either commercially available or may be prepared as described in the synthesis of intermediates A-G.

TABLE 3

The following compounds were prepared according to the general procedure of step 6 and 7 provided in Example 19. The starting materials are either commercially available or may be prepared as described in the synthesis of intermediates A-G.

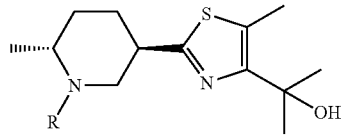

| Example | R | IUPAC Name | LRMS or HRMS (M + H⁺) |
|---|---|---|---|
| 20 | | (2-(2H-1,2,3-triazol-2-yl)thiophen-3-yl)((2R,5R)-5-(4-(2-hydroxypropan-2-yl)-5-methylthiazol-2-yl)-2-methylpiperidin-1-yl)methanone | Calc'd 432.1, found 432.1 |
| 21 | | (4-(2H-1,2,3-triazol-2-yl)thiophen-3-yl)((2R,5R)-5-(4-(2-hydroxypropan-2-yl)-5-methylthiazol-2-yl)-2-methylpiperidin-1-yl)methanone | Calc'd 432.1, found 432.1 |

TABLE 3-continued

The following compounds were prepared according to the general procedure of step 6 and 7 provided in Example 19. The starting materials are either commercially available or may be prepared as described in the synthesis of intermediates A-G.

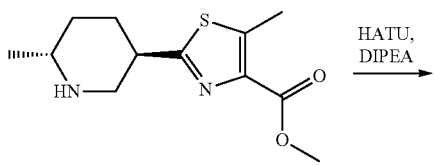

| Example | R | IUPAC Name | LRMS or HRMS (M + H+) |
|---|---|---|---|
| 22 | (structure: 4-fluoro-2-(2H-1,2,3-triazol-2-yl)phenyl group) | (4-fluoro-2-(2H-1,2,3-triazol-2-yl)phenyl)((2R,5R)-5-(4-(2-hydroxypropan-2-yl)-5-methylthiazol-2-yl)-2-methylpiperidin-1-yl)methanone | Calc'd 444.1, found 444.1 |

EXAMPLE 23

(4-(2H-1,2,3-Triazol-2-yl)thiophen-3-yl)((2R,5R)-5-(2-(2-hydroxypropan-2-yl)thiazol-4-yl)-2-methylpiperidin-1-yl)methanone

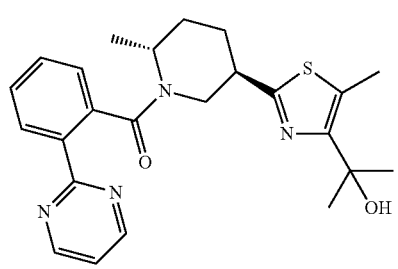

Step 1: Methyl 5-methyl-2-((3R,6R)-6-methyl-1-(2-(pyrimidin-2-yl)benzoyl)piperidin-3-yl)thiazole-4-carboxylate (29)

A solution of methyl 5-methyl-2-((3R,6R)-6-methylpiperidin-3-yl)thiazole-4-carboxylate (Example 19, Step 5) (64 mg, 0.25 mmol), HATU (143 mg, 0.38 mmol), DIPEA (97 mg, 0.75 mmol) and 2-(pyrimidin-2-yl)benzoic acid (50 mg, 0.25 mmol) in DCM (2 mL) was stirred at RT for 3 h. The reaction mixture was poured into water, extracted with DCM (50 mL×3), the combined organic layers washed with brine, dried over MgSO₄, filtered and concentrated in vacuo. The crude product was purified by Prep-TLC (50% EtOAc in petroleum ether) to give the title compound as a white solid. LRMS m/z (M+H) 437.1 found, 437.1 required.

Step 2: ((2R,5R)-5-(4-(2-Hydroxypropan-2-yl)-5-methylthiazol-2-yl)-2-methylpiperidin-1-yl)(2-(pyrimidin-2-yl)phenyl)methanone (Example 23)

To a solution of the product from step 1 (50 mg, 0.12 mmol) in dry THF (2 mL) at 0° C. under nitrogen atmosphere was added dropwise methylmagnesium bromide solution (0.5 mL, 3M, 1.5 mmol), the resulting mixture stirred at 0° C. for 1 h, and saturated aqueous ammonium chloride added. The mixture was extracted with EtOAc (50 mL×3), the combined organic layers washed with water and brine, dried over MgSO₄, filtered and concentrated in vacuo. The crude product was purified by Prep-HPLC to give the title compound as a white solid. LRMS m/z (M+H) 437.1 found, 437.1 required.

The following compounds were prepared according to the general procedure provided in Example 23. The starting materials are either commercially available or may be prepared as described in the synthesis of Intermediates A-G, or may be prepared from commercially available reagents using conventional reactions well known in the art.

TABLE 4

The following compounds were prepared according to the general procedure provided in Example 23. The starting materials are either commercially available or may be prepared as described in the synthesis of Intermediates A-G, or may be prepared from commercially available reagents using conventional reactions well known in the art.

| Example | R | IUPAC Name | LRMS or HRMS (M + H+) |
|---|---|---|---|
| 24 | 2-(2H-tetrazol-2-yl)phenyl carbonyl group | (2-(2H-Tetrazol-2-yl)phenyl)((2R,5R)-5-(4-(2-hydroxypropan-2-yl)-5-methylthiazol-2-yl)-2-methylpiperidin-1-yl)methanone | Calc'd 427.1, found 427.1 |
| 25 | 2-(1-cyanocyclopropyl)phenyl carbonyl group | 1-(2-((2R,5R)-5-(4-(2-Hydroxypropan-2-yl)-5-methylthiazol-2-yl)-2-methylpiperidine-1-carbonyl)phenyl)cyclopropanecarbonitrile | Calc'd 424.2, found 424.2 |
| 26 | 2-((methylsulfonyl)methyl)phenyl carbonyl group | ((2R,5R)-5-(4-(2-Hydroxypropan-2-yl)-5-methylthiazol-2-yl)-2-methylpiperidin-1-yl)(2-((methylsulfonyl)methyl)phenyl)methanone | Calc'd 451.1, found 451.1 |
| 27 | 2-(pyrimidin-2-yl)thiophen-3-yl carbonyl group | ((2R,5R)-5-(4-(2-Hydroxypropan-2-yl)-5-methylthiazol-2-yl)-2-methylpiperidin-1-yl)(2-(pyrimidin-2-yl)thiophen-3-yl)methanone | Calc'd 451.1, found 451.1 |
| 28 | 4-(pyrimidin-2-yl)thiophen-3-yl carbonyl group | ((2R,5R)-5-(4-(2-Hydroxypropan-2-yl)-5-methylthiazol-2-yl)-2-methylpiperidin-1-yl)(4-(pyrimidin-2-yl)thiophen-3-yl)methanone | Calc'd 443.1, found 443.1 |

EXAMPLE 29

(2-(2H-1,2,3-Triazol-2-yl)thiophen-3-yl)((2R,5R)-5-(2-(2-hydroxypropan-2-yl)thiazol-4-yl)-2-methylpiperidin-1-yl)methanone

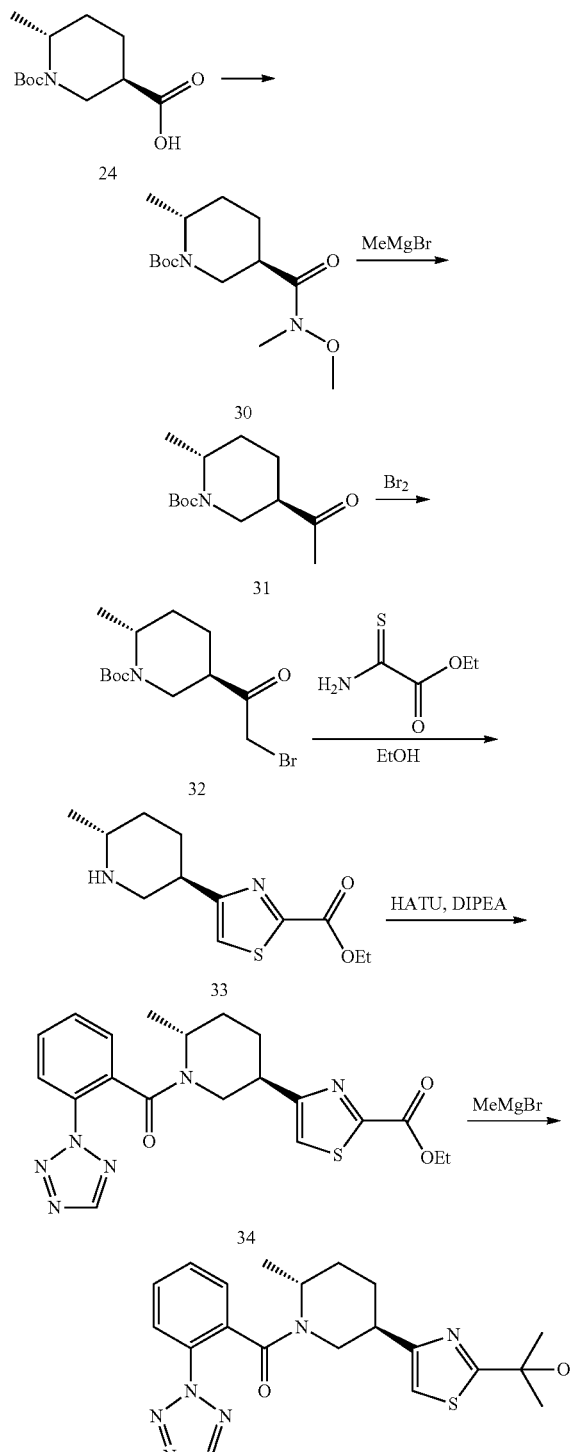

Example 29

Step 1: (2R,5R)-tert-Butyl 5-(methoxy(methyl)carbamoyl)-2-methylpiperidine-1-carboxylate (30)

To a solution of (3R,6R)-1-(tert-butoxycarbonyl)-6-methylpiperidine-3-carboxylic acid (Example 19, Step 2) (3.00 g, 12.3 mmol) in DCM (30 mL) was added HATU (9.4 g, 24.7 mmol), triethylamine (2.5 g, 24.7 mmol) and N,O-dimethylhydroxylamine hydrochloride (2.4 g, 24.7 mmol) and the mixture stirred at RT overnight. The reaction mixture was diluted with water (30 mL), extracted with DCM (200 mL×3), the combined organic layers washed with brine (200 mL×3), dried over $Na_2SO_4$, filtered and concentrated in vacuo. The crude product was purified by chromatography on silica (33% EtOAc in petroleum ether) to give the title compound. LRMS m/z (M+H) 287.2 found, 287.2 required.

Step 2: (2R,5R)-tert-Butyl 5-acetyl-2-methylpiperidine-1-carboxylate (31)

To a solution of the product from step 1 (600 mg, 2.1 mmol) in dry THF (10 mL) at 0° C. was added dropwise a solution of methylmagnesium bromide (5.0 mL, 3 M in ether) and the mixture stirred at 0° C. for 1 h. Water (20 mL) was added and the mixture extracted with EtOAc (100 mL×3). The combined organic layers were dried over $MgSO_4$, filtered and concentrated in vacuo. The crude product was purified by chromatography on silica (20% EtOAc in petroleum ether) to give the title compound as a colorless oil. LRMS m/z (M+H) 242.2 found, 242.2 required.

Step 3: (2R,5R)-tert-Butyl 5-(2-bromoacetyl)-2-methylpiperidine-1-carboxylate (32)

To a solution of the product from step 2 (200 mg, 0.83 mmol) in dry methanol (20 mL) was added calcium carbonate (100 mg) followed by dropwise addition of a solution of bromine (133 mg, 0.83 mmol) in methanol (5 mL). The resulting mixture was stirred at 60° C. for 8 h, cooled to RT, filtered, and the filtrate concentrated in vacuo to give the title compound as yellow oil. LRMS m/z (M+H) 320.1, 322.1 found, 320.1, 322.1 required.

Step 4: Ethyl 4-((3R,6R)-6-methylpiperidin-3-yl)thiazole-2-carboxylate (33)

To a solution of the product from step 3 (100 mg, 0.31 mmol) in dry ethanol (2 mL) was added ethyl 2-amino-2-thioxoacetate (50 mg, 0.37 mmol). The resulting mixture was stirred at 80° C. for 3 h., cooled to room temperature and concentrated in vacuo. The crude product was purified by Prep-TLC (50% EtOAc in petroleum ether) to give the title compound as an oil. LRMS m/z (M+H) 255.1 found, 255.1 required.

Step 5: Ethyl 4-((3R,6R)-6-methylpiperidin-3-yl)thiazole-2-carboxylate (34)

A solution of the product from step 4 (67 mg, 0.26 mmol), HATU (148 mg, 0.39 mmol), DIPEA (100.6 mg, 0.52 mmol) and 2-(2H-tetrazol-2-yl)benzoic acid (50 mg, 0.26 mmol) in DCM (2 mL) was stirred at RT for 3 h under nitrogen atmosphere, poured into water and extracted with DCM (50 mL×3). The combined organic layers were washed with brine, dried over $MgSO_4$, filtered and concentrated in vacuo. The crude product was purified by Prep-TLC (50% EtOAc in petroleum ether) to give the title compound as yellow oil. LRMS m/z (M+H) 427.2 found, 427.2 required.

Step 6: (2-(2H-Tetrazol-2-yl)phenyl)((2R,5R)-5-(2-(2-hydroxypropan-2-yl)thiazol-4-yl)-2-methylpiperidin-1-yl)methanone (Example 29)

To a solution of the product from step 5 (50 mg, 0.12 mmol) in dry THF (2 mL) at 0° C. under nitrogen atmosphere was added dropwise methylmagnesium bromide (0.5 mL), and the resulting mixture stirred at 0° C. for 1 h. Saturated aqueous ammonium chloride was added and the mixture extracted with EtOAc (50 mL×3). The combined organic layers were washed with water and brine, dried over MgSO$_4$, filtered, concentrated in vacua and the crude product purified by Prep-HPLC to give the title compound as a white solid. LRMS m/z (M+H) 413.1 found, 413.1 required.

The following compounds were prepared according to the general procedure provided in Example 29. The starting materials are either commercially available or may be prepared as described in the synthesis of Intermediates A-G, or may be prepared from commercially available reagents using conventional reactions well known in the art.

TABLE 5

The following compounds were prepared according to the general procedure provided in Example 29. The starting materials are either commercially available or may be prepared as described in the synthesis of Intermediates A-G, or may be prepared from commercially available reagents using conventional reactions well known in the art.

| Example | R | IUPAC Name | LRMS or HRMS (M + H$^+$) |
|---|---|---|---|
| 30 | | 1-(2-((2R,5R)-5-(2-(2-hydroxypropan-2-yl)thiazol-4-yl)-2-methylpiperidine-1-carbonyl)phenyl)cyclopropanecarbonitrile | Calc'd 410.2, found 410.2 |
| 31 | | ((2R,5R)-5-(2-(2-hydroxypropan-2-yl)thiazol-4-yl)-2-methylpiperidin-1-yl)(2-(pyrimidin-2-yl)thiophen-3-yl)methanone | Calc'd 429.1, found 429.1 |
| 32 | | ((2R,5R)-5-(2-(2-hydroxypropan-2-yl)thiazol-4-yl)-2-methylpiperidin-1-yl)(4-(pyrimidin-2-yl)thiophen-3-yl)methanone | Calc'd 429.1, found 429.1 |

TABLE 5-continued

The following compounds were prepared according to the general procedure provided in Example 29. The starting materials are either commercially available or may be prepared as described in the synthesis of Intermediates A-G, or may be prepared from commercially available reagents using conventional reactions well known in the art.

| Example | R | IUPAC Name | LRMS or HRMS (M + H⁺) |
|---|---|---|---|
| 33 | | ((2R,5R)-5-(2-(2-hydroxypropan-2-yl)thiazol-4-yl)-2-methylpiperidin-1-yl)(2-(pyrimidin-2-yl)phenyl)methanone | Calc'd 423.1, found 423.1 |
| 34 | | ((2R,5R)-5-(2-(2-hydroxypropan-2-yl)thiazol-4-yl)-2-methylpiperidin-1-yl)(2-((methylsulfonyl)methyl)phenyl)methanone | Calc'd 437.1, found 437.1 |

EXAMPLE 35

(4-(2H-1,2,3-triazol-2-yl)thiophen-3-yl)((2R,5R)-5-(2-(2-hydroxypropan-2-yl)thiazol-4-yl)-2-methylpiperidin-1-yl)methanone

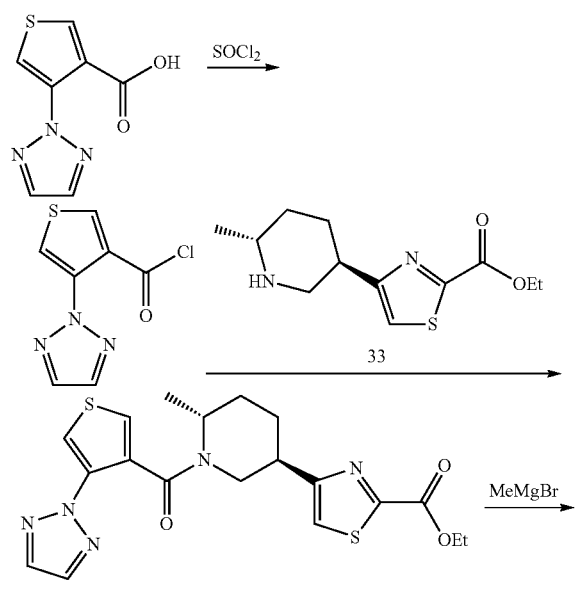

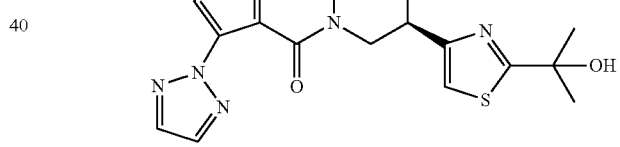

Example 35

Step 1: Ethyl 4-((3R,6R)-1-(4-(2H-1,2,3-triazol-2-yl)thiophene-3-carbonyl)-6-methylpiperidin-3-yl)thiazole-2-carboxylate (32)

A solution of 4-(2H-1,2,3-triazol-2-yl)thiophene-3-carboxylic acid (Intermediate F) (50 mg, 0.26 mmol) in thionyl chloride (2 mL) was stirred at 80° C. for 1 h, cooled to RT and concentrated in vacuo. The residue was dissolved in DCM (10 mL) and added to a solution of ethyl 4-((3R,6R)-6-methylpiperidin-3-yl)thiazole-2-carboxylate (Example 29, step 4) (56 mg, 0.26 mmol) in DCM (1 mL) and DIPEA (0.1 mL) at 0° C. and the resulting mixture stirred at RT for 12 h. The mixture was poured into water and extracted with EtOAc (50 mL×3), the combined organic layers washed with brine, dried over MgSO₄, filtered and concentrated in vacua. The crude product was purified by Prep-TLC (50% EtOAc in petroleum ether) to give the title compound as a white solid. LRMS m/z (M+H) 432.1 found, 432.1 required.

Step 2: (4-(2H-1,2,3-Triazol-2-yl)thiophen-3-yl)
((2R,5R)-5-(2-(2-hydroxypropan-2-yl)thiazol-4-yl)-
2-methylpiperidin-1-yl)methanone (Example 35)

To a solution of the product from step 1 (50 mg, 0.12 mmol) in dry THF (2 mL) at 0° C. under nitrogen atmosphere was added dropwise methylmagnesium bromide (0.5 mL, 3M, 1.5 mmol) and the resulting mixture stirred at 0° C. for 1 h. Saturated aqueous ammonium chloride was added and the mixture extracted with EtOAc (50 mL×3). The combined organic layers were washed with water and brine, dried over MgSO$_4$, filtered, and concentrated in vacua. The crude product was purified by Prep-HPLC to give the title compound as a white solid. LRMS m/z (M+H) 418.1 found, 418.1 required.

EXAMPLE 36

(2-(2H-1,2,3-triazol-2-yl)phenyl)((2R,5R)-5-(2-(2-hydroxypropan-2-yl)thiazol-4-yl)-2-methylpiperidin-1-yl)methanone

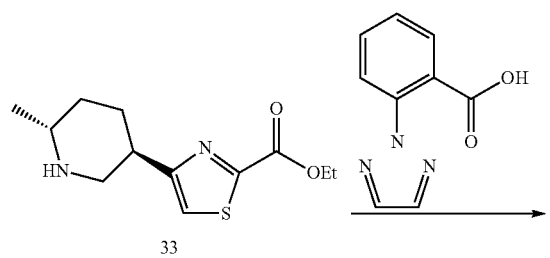

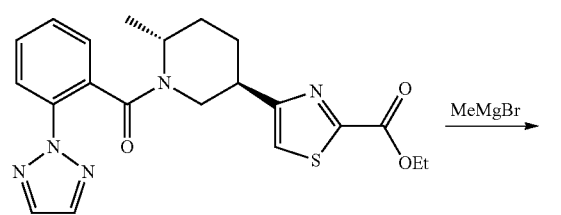

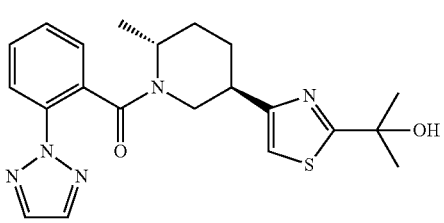

Example 36

Step 1: ethyl 4-((3R,6R)-1-(2-(2H-1,2,3-triazol-2-yl)benzoyl)-6-methylpiperidin-3-yl)thiazole-2-carboxylate (36)

A solution of 2-(2H-1,2,3-triazol-2-yl)benzoic acid (250 mg, 1.32 mmol) in thionyl chloride (5 mL) was stirred at 80° C. for 1 h, cooled to RT and concentrated in vacuo. The residue was dissolved in DCM (1.0 mL) and added to a solution of piperidine intermediate 33 (Example 29, Step 4) (337 mg, 1.32 mmol) in DCM (3.0 mL) and DIPEA (341 mg, 2.64 mmol) at 0° C. The resulting mixture was stirred at RT for 12 h, poured into water and extracted with EtOAc (50 mL×3). The combined organic layers were washed with brine, dried over MgSO$_4$, filtered and concentrated in vacuo. The crude product was purified by Prep-TLC (50% EtOAc in petroleum ether) to give the title compound as a white solid. LRMS m/z (M+H) 426.2 found, 426.2 required.

Step 2: (2-(2H-1,2,3-Triazol-2-yl)phenyl)((2R,5R)-5-(2-(2-hydroxypropan-2-yl)thiazol-4-yl)-2-methylpiperidin-1-yl)methanone (Example 36)

To a solution of the product from step 1 (110 mg, 0.26 mmol) in dry THF (2.0 mL) at 0° C. under nitrogen atmosphere was added, dropwise, 3M methylmagnesium bromide solution (2.0 mL). The resulting mixture was stirred at 0° C. for 1 h, saturated aqueous ammonium chloride added and the mixture extracted with EtOAc (50 mL×3). The combined organic layers were washed with water and brine, dried over MgSO$_4$, filtered and concentrated in vacuo. The crude product was purified by Prep-HPLC to give the title compound as a white solid. LRMS m/z (M+H) 412.1 found, 412.1 required.

EXAMPLE 37

(2-(2H-1,2,3-Triazol-2-yl)thiophen-3-yl)((2R,5R)-5-(2-(2-hydroxypropan-2-yl)thiazol-4-yl)-2-methylpiperidin-1-yl)methanone

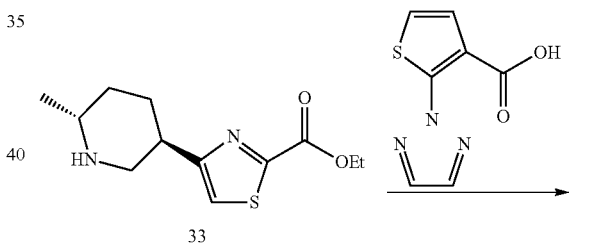

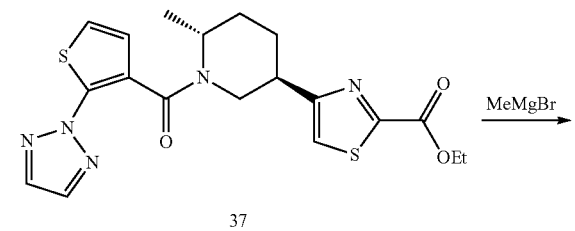

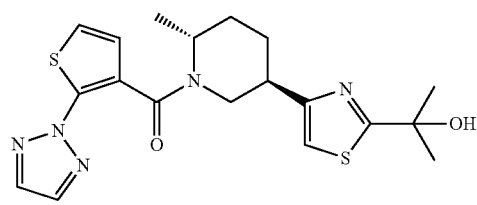

Example 37

Step 1: Ethyl 4-((3R,6R)-1-(2-(2H-1,2,3-triazol-2-yl)thiophene-3-carbonyl)-6-methylpiperidin-3-yl)thiazole-2-carboxylate (37)

A solution of 2-(2H-1,2,3-triazol-2-yl)thiophene-3-carboxylic acid (Intermediate D) (50 mg, 0.26 mmol) in thionyl chloride (2.0 mL) was stirred at 80° C. for 1 h, cooled to RT and concentrated in vacuo. The residue was dissolved in DCM (0.5 mL) and added to a solution of ethyl 4-((3R,6R)-6-methylpiperidin-3-yl)thiazole-2-carboxylate (Example 29, Step 4) (66.3 mg, 0.26 mmol) in DCM (1.5 mL) and DIPEA (100.6 mg, 0.78 mmol) at 0° C. The resulting mixture was stirred at RT for 2 h, poured into water and extracted with EtOAc (50 mL×3). The combined organic layers were washed with brine, dried over MgSO$_4$, filtered and concentrated in vacuo. The crude product was purified by Prep-TLC (50% EtOAc in petroleum ether) to give the title compound as a white solid. LRMS m/z (M+H) 432.1 found, 432.1 required.

Step 2: (2-(2H-1,2,3-Triazol-2-yl)phenyl)((2R,5R)-5-(2-(2-hydroxypropan-2-yl)thiazol-4-yl)-2-methylpiperidin-1-yl)methanone (Example 37)

To a solution of the product from step 1 (150 mg, 0.35 mmol) in dry THF (3.0 mL) at 0° C. under nitrogen atmosphere was added 3M of methylmagnesium bromide solution (0.5 mL) dropwise. The resulting mixture was stirred at 0° C. for 1 h, quenched with saturated aqueous ammonium chloride and extracted with EtOAc (50 mL×3). The combined organic layers were washed with water and brine, dried over MgSO$_4$, filtered, and concentrated in vacuum. The residue was purified by Prep-HPLC to give the title compound (80 mg) as white solid. LRMS m/z (M+H) 418.1 found, 418.1 required.

The following compound was prepared according to the general procedure provided in Example 35. The starting materials are either commercially available or may be prepared as described in the synthesis of intermediates A-G, or may be prepared from commercially available reagents using conventional reactions well known in the art.

TABLE 7

The following table shows representative data for the compounds of the Examples as orexin receptor antagonists as determined by the FLIPR Ca$^{2+}$ Flux Assay (Okumura et al., *Biochem. Biophys. Res. Comm.*, 2001, 280: 976-981.) Chinese hamster ovary (CHO) cells expressing the human orexin-1 receptor (hOX1R) or the human orexin-2 receptor (hOX2R) were grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells were seeded at ~20,000 cells/well into Becton-Dickinson black 384-well clear bottom sterile plates coated with poly-D-lysine. All reagents were from GIBCO-Invitrogen Corp. The seeded plates were incubated overnight at 37° C. and 5% CO$_2$. Ala-6,12 human orexin-A, used as the agonist, was prepared as a 1 mM stock solution in 1% bovine serum albumin (BSA) and diluted in assay buffer (HBSS containing 20 mM HEPES, 0.1% BSA and 2.5 mM probenecid, pH 7.4) for use in the assay at a final concentration of 70 pM. Test compounds were prepared as 10 mM stock solution in DMSO, then diluted in 384-well plates, first in DMSO, then assay buffer.

On the day of the assay, cells were washed 3X with 100 µl assay buffer and then incubated for 60 minutes (37° C., 5% CO$_2$) in 60 µl assay buffer containing 1 µM Fluo-4AM ester, 0.02% pluorinic acid, and 1% BSA. The dye loading solution was then aspirated and cells were washed 3X with 100 µl assay buffer. 30 µl of that same buffer was left in each well. Within the Fluorescent Imaging Plate Reader (FLIPR, Molecular Devices), test compounds were added to the plate in a volume of 25 µl, incubated for 5 minutes, and then 25 µl of agonist was added. Fluorescence was measured for each well at 1 second intervals for 5 minutes, and the height of each fluorescence peak was compared to the height of the fluorescence peak induced by 70 pM of Ala-6,12 orexin-A with buffer in place of test compound. For each test compound, IC$_{50}$ value (the concentration of test compound needed to inhibit 50% of the agonist response) was determined.

| Example | hOX2R FLIPR IC$_{50}$ (nM) | hOX1R FLIPR IC$_{50}$ (nM) |
| --- | --- | --- |
| 1 | 1509 | >10000 |
| 2 | 67 | >10000 |
| 3 | 2650 | >10000 |
| 4 | 50 | >10000 |
| 5 | 17 | 2250 |
| 6 | 165 | 10000 |
| 7 | 15 | 360 |
| 8 | 133 | >10000 |
| 9 | 9.4 | 520 |
| 10 | 19 | 7400 |
| 11 | 15 | 950 |
| 12 | 44 | >10000 |

TABLE 6

The following compounds were prepared according to the general procedure provided in Example 35. The starting materials are either commercially available or may be prepared as described in the synthesis of Intermediates A-G, or may be prepared from commercially available reagents using conventional reactions well known in the art.

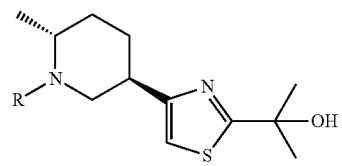

| Example | R | IUPAC Name | LRMS or HRMS (M + H$^+$) |
| --- | --- | --- | --- |
| 38 | (structure: 4-fluoro-2-(2H-1,2,3-triazol-2-yl)phenyl group) | (4-Fluoro-2-(2H-1,2,3-triazol-2-yl)phenyl)((2R,5R)-5-(2-(2-hydroxypropan-2-yl)thiazol-4-yl)-2-methylpiperidin-1-yl)methanone | Calc'd 430.1, found 430.1 |

TABLE 7-continued

| | | |
|---|---|---|
| 13 | 19 | 2250 |
| 14 | 21 | >10000 |
| 15 | 16 | >10000 |
| 16 | 25 | 1000 |
| 17 | 29 | 5470 |
| 18 | 114 | >10000 |
| 19 | 14 | 330 |
| 20 | 12 | 970 |
| 21 | 30 | 2800 |
| 22 | 20 | 930 |
| 23 | 27 | 600 |
| 24 | 19 | 2650 |
| 25 | 12 | 240 |
| 26 | 32 | >10000 |
| 27 | 87 | 700 |
| 28 | 29 | 900 |
| 29 | 15 | > |
| 30 | 13 | 1200 |
| 31 | 90 | >10000 |
| 32 | 130 | >10000 |
| 33 | 102 | >10000 |
| 34 | 40 | >10000 |
| 35 | 14 | >10000 |
| 36 | 20 | 2300 |
| 37 | 16 | 7200 |
| 38 | 14 | 2050 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of formula I:

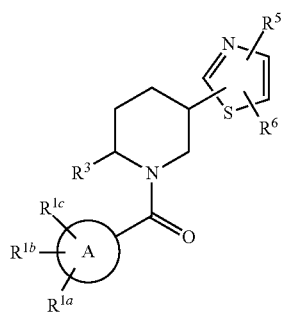

wherein:
A is selected from the group consisting of phenyl, naphthyl and heteroaryl;
$R^{1a}$, $R^{1b}$ and $R^{1c}$ are independently selected from the group consisting of:
  (1) hydrogen,
  (2) halogen,
  (3) hydroxyl,
  (4) —(C=O)$_m$—O$_n$—C$_{1-6}$alkyl, where the alkyl is unsubstituted or substituted with one or more substituents selected from $R^4$,
  (5) —(C=O)$_m$—O$_n$—C$_{3-6}$cycloalkyl, where the cycloalkyl is unsubstituted or substituted with one or more substituents selected from $R^4$,
  (6) —(C=O)$_m$—C$_{2-4}$alkenyl, where the alkenyl is unsubstituted or substituted with one or more substituents selected from $R^4$,
  (7) —(C=O)$_m$—C$_{2-4}$alkynyl, where the alkynyl is unsubstituted or substituted with one or more substituents selected from $R^4$,
  (8) —(C=O)$_m$—O$_n$-phenyl or —(C=O)$_m$—O$_n$-naphthyl, where the phenyl or naphthyl is unsubstituted or substituted with one or more substituents selected from $R^4$,
  (9) —(C=O)$_m$—O$_n$-heterocycle, where the heterocycle is unsubstituted or substituted with one or more substituents selected from $R^4$,
  (10) —(C=O)$_m$—NR$^9$R$^{10}$;
  (11) —S(O)$_2$—NR$^9$R$^{10}$,
  (12) —(CH$_2$)$_r$—S(O)$_q$—R$^9$, where r is 0, 1 or 2 (wherein if r is 0, a bond is present), q is 0, 1 or 2 and
  (13) —CO$_2$H,
  (14) —CN, and
  (15) —NO$_2$;
$R^3$ is selected from C$_{1-6}$alkyl and C$_{3-6}$cycloalkyl, which is unsubstituted or substituted with one or more substituents selected from $R^4$;
$R^4$ is selected from the group consisting of:
  (1) hydroxyl,
  (2) halogen,
  (3) C$_{1-6}$alkyl,
  (4) —C$_{3-6}$cycloalkyl,
  (5) —O—C$_{1-6}$alkyl,
  (6) —O(C=O)—C$_{1-6}$alkyl,
  (7) —NH$_2$,
  (8) —NH—C$_{1-6}$alkyl,
  (9) —NO$_2$,
  (10) phenyl,
  (11) heterocycle,
  (12) —CO$_2$H, and
  (13) —CN;
$R^5$ and $R^6$ are independently selected from the group consisting of:
  (1) hydrogen,
  (2) halogen,
  (3) C$_{1-6}$alkyl, which is unsubstituted or substituted with halogen, hydroxyl, —O—C$_{1-6}$ alkyl, —NR$^7$R$^8$, —(C=O)O—C$_{1-6}$alkyl or phenyl,
  (4) C$_{3-6}$cycloalkyl, which is unsubstituted or substituted with C$_{1-6}$alkyl, halogen or hydroxyl,
  (6) —(C=O)O—C$_{1-6}$alkyl, which is unsubstituted or substituted with halogen, hydroxyl or phenyl
  (7) —CN, and
  (8) —(C=O)NR$^7$R$^8$;
$R^7$ and $R^8$ are independently hydrogen or C$_{1-6}$alkyl;
$R^9$ and $R^{10}$ are independently selected from the group consisting of:
  (1) hydrogen,
  (2) C$_{1-6}$alkyl, which is unsubstituted or substituted with $R^4$,
  (3) C$_{3-6}$alkenyl, which is unsubstituted or substituted with $R^4$,
  (4) C$_{3-6}$alkynyl, which is unsubstituted or substituted with $R^4$,
  (5) C$_{3-6}$cycloalkyl which is unsubstituted or substituted with $R^4$,
  (6) phenyl, which is unsubstituted or substituted with $R^4$, and
  (7) heterocycle, which is unsubstituted or substituted with $R^4$,
m and n are independently 0 or 1 (wherein if m is 0 or n is 0, a bond is present);
r is 0, 1 or 2 (wherein if r is 0, a bond is present);
q is 0, 1 or 2;
or a pharmaceutically acceptable salt thereof.

2. The compound of claim 1 or a pharmaceutically acceptable salt thereof, wherein A is phenyl.

3. The compound of claim 1 or a pharmaceutically acceptable salt thereof, wherein A is thiophenyl.

4. The compound of claim 1 of formula Id:

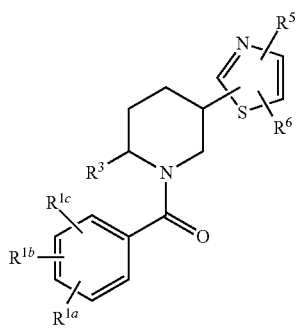

Id or a pharmaceutically acceptable salt thereof.

5. The compound of claim 1 of formula Io:

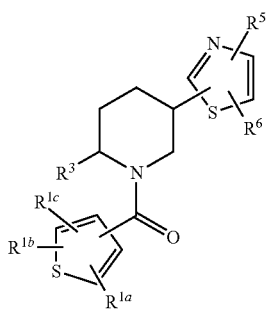

Io or a pharmaceutically acceptable salt thereof.

6. The compound of claim 1 or a pharmaceutically acceptable salt thereof, wherein $R^{1a}$, $R^{1b}$ and $R^{1c}$ are independently selected from the group consisting of:
(1) hydrogen,
(2) halogen,
(3) —O—$CH_2$—$CH_3$, which is unsubstituted or substituted with halogen,
(4) —(C=O)—O—$C_{1-6}$alkyl, which is unsubstituted or substituted with halogen,
(5) cyclopropyl, which is unsubstituted or substituted with halogen, hydroxyl, or —CN,
(6) —$CH_2$—$S(O)_2$—$C_{1-6}$alkyl, and
(7) heteroaryl, wherein heteroaryl is selected from triazolyl, tetrazolyl, oxazolyl, pyrrolyl, imidazolyl, indolyl, pyridyl, and pyrimidinyl.

7. The compound of claim 1 or a pharmaceutically acceptable salt thereof, wherein $R^{1a}$ is hydrogen, $R^{1b}$ is hydrogen or halogen, and $R^{1c}$ is heteroaryl, where said heteroaryl is selected from triazolyl, tetrazolyl, oxazolyl, pyrrolyl, imidazolyl, indolyl, pyridyl, and pyrimidinyl.

8. The compound of claim 1 or a pharmaceutically acceptable salt thereof, wherein $R^3$ is methyl.

9. The compound of claim 1 or a pharmaceutically acceptable salt thereof, wherein $R^5$ and $R^6$ are independently selected from the group consisting of:

(1) hydrogen,
(2) halogen,
(3) $C_{1-6}$alkyl,
(4) trifluoromethyl,
(5) $CHF_2$,
(6) —(C=O)O—$C_{1-6}$alkyl, and (7) 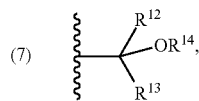

where $R^{12}$ and $R^{13}$ are independently hydrogen or $C_{1-2}$alkyl (optionally substituted with fluoro), and $R^{14}$ is hydrogen or $C_{1-6}$alkyl.

10. The compound of claim 1 or a pharmaceutically acceptable salt thereof, wherein $R^5$ is hydrogen, and $R^6$ is

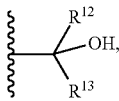

wherein $R^{12}$ and $R^{13}$ are independently hydrogen, methyl, —$CHF_2$ or $CF_3$.

11. The compound of claim 10 or a pharmaceutically acceptable salt thereof, wherein $R^{12}$ and $R^{13}$ are both methyl.

12. A compound that is selected from the group consisting of:
ethyl 2-((3R,6R)-1-(2-(2H-1,2,3-triazol-2-yl)benzoyl)-6-methylpiperidin-3-yl)thiazole-5-carboxylate;
(2-(2H-1,2,3-triazol-2-yl)phenyl)((2R,5R)-5-(5-(2-hydroxypropan-2-yl)thiazol-2-yl)-2-methylpiperidin-1-yl)methanone;
(2-(2H-1,2,3-triazol-2-yl)phenyl)((2R,5S)-5-(5-(2-hydroxypropan-2-yl)thiazol-2-yl)-2-methylpiperidin-1-yl)methanone;
(2-(2H-1,2,3-triazol-2-yl)phenyl)((2R,5R)-5-(2-(2-hydroxypropan-2-yl)thiazol-5-yl)-2-methylpiperidin-1-yl)methanone;
(2-(2H-1,2,3-triazol-2-yl)phenyl)((2R,5R)-5-(4-(2-hydroxypropan-2-yl)thiazol-2-yl)-2-methylpiperidin-1-yl)methanone;
(2-(2H-1,2,3-triazol-2-yl)phenyl)((2R,5R)-2-methyl-5-(4-((S)-2,2,2-trifluoro-1-hydroxyethyl)thiazol-2-yl)piperidin-1-yl)methanone;
(2-(2H-1,2,3-triazol-2-yl)phenyl)((2R,5R)-2-methyl-5-(4-((S)-2,2,2-trifluoro-1-hydroxyethyl)thiazol-2-yl)piperidin-1-yl)methanone;
(2-(2H-1,2,3-triazol-2-yl)phenyl)((2R,5R)-5-(4-((R)-2,2-difluoro-1-hydroxyethyl)thiazol-2-yl)-2-methylpiperidin-1-yl)methanone;
(2-(2H-1,2,3-triazol-2-yl)phenyl)((2R,5R)-5-(4-((S)-2,2-difluoro-1-hydroxyethyl)thiazol-2-yl)-2-methylpiperidin-1-yl)methanone;
(2-(2H-1,2,3-triazol-2-yl)thiophen-3-yl)((2R,5R)-5-(4-(2-hydroxypropan-2-yl)thiazol-2-yl)-2-methylpiperidin-1-yl)methanone;
1-(2-((2R,5R)-5-(4-(2-hydroxypropan-2-yl)thiazol-2-yl)-2-methylpiperidine-1-carbonyl)phenyl)cyclopropanecarbonitrile;
methyl 2-((2R,5R)-5-(4-(2-hydroxypropan-2-yl)thiazol-2-yl)-2-methylpiperidine-1-carbonyl)benzoate;
(4-fluoro-2-(2H-1,2,3-triazol-2-yl)phenyl)((2R,5R)-5-(4-(2-hydroxypropan-2-yl)thiazol-2-yl)-2-methylpiperidin-1-yl)methanone;

(2-(2H-tetrazol-2-yl)phenyl)((2R,5R)-5-(4-(2-hydroxypropan-2-yl)thiazol-2-yl)-2-methylpiperidin-1-yl)methanone;

(4-(2H-1,2,3-triazol-2-yl)thiophen-3-yl)((2R,5R)-5-(4-(2-hydroxypropan-2-yl)thiazol-2-yl)-2-methylpiperidin-1-yl)methanone;

((2R,5R)-5-(4-(2-hydroxypropan-2-yl)thiazol-2-yl)-2-methylpiperidin-1-yl)(4-(pyrimidin-2-yl)thiophen-3-yl)methanone;

((2R,5R)-5-(4-(2-hydroxypropan-2-yl)thiazol-2-yl)-2-methylpiperidin-1-yl)(2-(pyrimidin-2-yl)phenyl)methanone;

((2R,5R)-5-(4-(2-hydroxypropan-2-yl)thiazol-2-yl)-2-methylpiperidin-1-yl)(2-(pyrimidin-2-yl)thiophen-3-yl)methanone;

(2-(2H-1,2,3-triazol-2-yl)phenyl)((2R,5R)-5-(4-(2-hydroxypropan-2-yl)-5-methylthiazol-2-yl)-2-methylpiperidin-1-yl)methanone;

(2-(2H-1,2,3-triazol-2-yl)thiophen-3-yl)((2R,5R)-5-(4-(2-hydroxypropan-2-yl)-5-methylthiazol-2-yl)-2-methylpiperidin-1-yl)methanone;

(4-(2H-1,2,3-triazol-2-yl)thiophen-3-yl)((2R,5R)-5-(4-(2-hydroxypropan-2-yl)-5-methylthiazol-2-yl)-2-methylpiperidin-1-yl)methanone;

(4-fluoro-2-(2H-1,2,3-triazol-2-yl)phenyl)((2R,5R)-5-(4-(2-hydroxypropan-2-yl)-5-methylthiazol-2-yl)-2-methylpiperidin-1-yl)methanone;

(4-(2H-1,2,3-triazol-2-yl)thiophen-3-yl)((2R,5R)-5-(2-(2-hydroxypropan-2-yl)thiazol-4-yl)-2-methylpiperidin-1-yl)methanone;

(2-(2H-tetrazol-2-yl)phenyl)((2R,5R)-5-(4-(2-hydroxypropan-2-yl)-5-methylthiazol-2-yl)-2-methylpiperidin-1-yl)methanone;

1-(2-((2R,5R)-5-(4-(2-hydroxypropan-2-yl)-5-methylthiazol-2-yl)-2-methylpiperidine-1-carbonyl)phenyl)cyclopropanecarbonitrile;

((2R,5R)-5-(4-(2-hydroxypropan-2-yl)-5-methylthiazol-2-yl)-2-methylpiperidin-1-yl)(2-((methylsulfonyl)methyl)phenyl)methanone;

((2R,5R)-5-(4-(2-hydroxypropan-2-yl)-5-methylthiazol-2-yl)-2-methylpiperidin-1-yl)(2-(pyrimidin-2-yl)thiophen-3-yl)methanone;

((2R,5R)-5-(4-(2-hydroxypropan-2-yl)-5-methylthiazol-2-yl)-2-methylpiperidin-1-yl)(4-(pyrimidin-2-yl)thiophen-3-yl)methanone;

(2-(2H-1,2,3-triazol-2-yl)thiophen-3-yl)((2R,5R)-5-(2-(2-hydroxypropan-2-yl)thiazol-4-yl)-2-methylpiperidin-1-yl)methanone;

1-(2-((2R,5R)-5-(2-(2-hydroxypropan-2-yl)thiazol-4-yl)-2-methylpiperidine-1-carbonyl)phenyl)cyclopropanecarbonitrile;

((2R,5R)-5-(2-(2-hydroxypropan-2-yl)thiazol-4-yl)-2-methylpiperidin-1-yl)(2-(pyrimidin-2-yl)thiophen-3-yl)methanone;

((2R,5R)-5-(2-(2-hydroxypropan-2-yl)thiazol-4-yl)-2-methylpiperidin-1-yl)(4-(pyrimidin-2-yl)thiophen-3-yl)methanone;

((2R,5R)-5-(2-(2-hydroxypropan-2-yl)thiazol-4-yl)-2-methylpiperidin-1-yl)(2-(pyrimidin-2-yl)phenyl)methanone;

((2R,5R)-5-(2-(2-hydroxypropan-2-yl)thiazol-4-yl)-2-methylpiperidin-1-yl)(2-((methylsulfonyl)methyl)phenyl)methanone;

(4-(2H-1,2,3-triazol-2-yl)thiophen-3-yl)((2R,5R)-5-(2-(2-hydroxypropan-2-yl)thiazol-4-yl)-2-methylpiperidin-1-yl)methanone;

(2-(2H-1,2,3-triazol-2-yl)phenyl)((2R,5R)-5-(2-(2-hydroxypropan-2-yl)thiazol-4-yl)-2-methylpiperidin-1-yl)methanone;

(2-(2H-1,2,3-triazol-2-yl)thiophen-3-yl)((2R,5R)-5-(2-(2-hydroxypropan-2-yl)thiazol-4-yl)-2-methylpiperidin-1-yl)methanone;

(4-fluoro-2-(2H-1,2,3-triazol-2-yl)phenyl)((2R,5R)-5-(2-(2-hydroxypropan-2-yl)thiazol-4-yl)-2-methylpiperidin-1-yl)methanone;

or a pharmaceutically acceptable salt thereof.

13. A pharmaceutical composition that comprises an inert carrier and a compound of claim 1 or a pharmaceutically acceptable salt thereof.

14. A method for treating insomnia in a mammalian patient in need thereof which comprises administering to the patient a therapeutically effective amount of the compound of claim 1 or a pharmaceutically acceptable salt thereof.

* * * * *